US007410638B1

(12) United States Patent
Zhang et al.

(10) Patent No.: US 7,410,638 B1
(45) Date of Patent: Aug. 12, 2008

(54) BACTERIAL STRAINS, GENES AND ENZYMES FOR CONTROL OF BACTERIAL DISEASES BY QUENCHING QUORUM-SENSING SIGNALS

(75) Inventors: Lianhui Zhang, Singapore (SG); Yihu Dong, Singapore (SG); Haibao Zhang, Singapore (SG); Jinling Xu, Singapore (SG)

(73) Assignee: Institute of Molecular Agrobiology, Singapore (SG)

( * ) Notice: Subject to any disclaimer, the term of this patent is extended or adjusted under 35 U.S.C. 154(b) by 526 days.

(21) Appl. No.: 10/362,569

(22) PCT Filed: Aug. 23, 2000

(86) PCT No.: PCT/SG00/00123

§ 371 (c)(1), (2), (4) Date: Jul. 21, 2003

(87) PCT Pub. No.: WO02/16623

PCT Pub. Date: Feb. 28, 2002

(51) Int. Cl.

| | |
|---|---|
| ***C12N 9/54*** | (2006.01) |
| ***C12N 15/00*** | (2006.01) |
| ***C12N 1/20*** | (2006.01) |
| ***C07H 21/04*** | (2006.01) |
| ***A61K 38/48*** | (2006.01) |

(52) U.S. Cl. .............. 424/94.64; 435/320.1; 435/252.3; 435/220; 435/325; 536/23.2

(58) Field of Classification Search ................. 435/220, 435/320.1, 252.33; 536/23.2; 424/94.64

See application file for complete search history.

(56) References Cited

OTHER PUBLICATIONS

Matthysse A. G. et al. A region of the *Agrobacterium tumefaciens* chromosome containing genes required for virulence and attachment to host cells, Biochem. Biophys. Acta, 1490, 208, 212, Jan. 31, 2000.*

GenBank Accession No. Q9WWD3, created Nov. 1, 1999.*

Dong Yi-Hu et al. AiiA, an enzyme that inactivates the acylhomoserine lactone quorum-sensing signal and attenuates the virulence of *Erwinia carotovora,* Proc. Natl. Acad. Sci. USA, 97, 3526-3531, Mar. 28, 2000.*

Mathysse A.G. Characterisation of Nonattaching Mutants of *Agrobacterium tumefaciens,* J. Bacteriol. 169, 313-323, 1997.*

* cited by examiner

*Primary Examiner*—Rebecca E. Prouty
*Assistant Examiner*—Malgorzata A. Walicka
(74) *Attorney, Agent, or Firm*—Rothwell, Figg, Ernst & Manbeck, P.C.

(57) ABSTRACT

The present invention relates to isolated nucleic acid molecules encoding an autoinducer inactivation protein, wherein the encoded protein comprises an amino acid sequence selected from the group consisting of $^{104}$HXHXDH$^{109}$~60aa~H$^{169}$~21aa~D$^{191}$ and $^{103}$HXHXDH$^{108}$~72aa~H$^{180}$~21aa~D$^{202}$, and to expression vectors and transformed plant and animal cells comprising the same. The proteins encoded by these nucleic acid molecules provide to a susceptible plant or animal increased resistance to a disease the virulence of which is regulated by autoinducers. Also provided are methods of increasing disease resistance in susceptible plants and animals.

10 Claims, 16 Drawing Sheets

| CLONES | ACTIVITY | | |
|---|---|---|---|
| pBM103-160 | + | 160 ———————————— 1360 | |
| pBM103-280 | + | 230 ———————— 1106 | |
| pBM103-230 | + | p lac → 280 ———————— 1106 | |
| pBM103-296 | + | 296 ———————— 1106 | |
| pKM103-310 | + | 310 ———————— 1106 | |
| pKM103-320 | − | p tac → 320 ———————— 1106 | |
| pKM103-330 | − | 330 ———————— 1106 | |
| pKM103-336 | − | 336 ———————— 1106<br>GTG      TAA | |
| pKM103-315 | + | 315 ———————— 1106<br>aiiB ORF | |

PstI
-314 CTGCAGCGTCGCTT -300
TATGCGGAGCTTGCCGACGTGCTGGGTGTTCCGGGTGAAGGGGATGCGGCAACCCGTTCG -240
GATGCGTTCGTTCAGCATATGGAAACGCTGATGGACGAAAGCGGCGCGCCGCGACGTCTG -180
CGCGATGTCGGCGTGACGGACAACACGCTCGCCATGCTTGCGTCCGACGCAATGAAACAG -120
AGCCGTCTGTTGGTCAATAATCCGGTCGAAGTCCGCGAAGAGGATGCGCTTGCGCTCTAC -60
CGCGAGGCGTTCTGACCCATTTCTGACAGCAATATCTTCAGTCCCAAGGGAGGAAAACGA -1
SD

GTGACCGATATCAGACTTTACATGCTTCAGTCGGGTACGCTGAAATGCAAGGTACACAAC 60
start

ATCAAGATGAACCAGGGGAACGGTGCAGACTATGAGATCCCCGTTCCGTTTTTCCTGATT 120
ACCCATCCGGGCGGGCACACCGTGATCGACGGCGGCAACGCGATTGAAGTTGCAACGGAT 180
CCGCGTGGCCATTGGGGCGGCATCTGCGATGTCTATTGGCCAGTGCTGGACAAGGACCAG 240
GGCTGCGTTGACCAGATCAAGGCGCTTGGTTTCGATCCGGCCGATGTCAAGTATGTTGTG 300
CAGTCGCACCTGCATCTCGATCATACCGGCGCCATCGGTCGCTTCCCCAACGCAACCCAC 360
ATCGTGCAGCGCTCGGAATATGAGTATGCCTTCACGCCCGACTGGTTTGCCGGTGGCGGC 420
TATATCCGCAAGGACTTCGACAAGCCGGGCCTGAAGTGGCAGTTCCTCAACGGTACGCAG 480
GACGACTATTACGACGTTTACGGCGACGGCACGCTCACCACGATCTTCACGCCCGGTCAT 540
GCGCCCGGCCACCAGTCCTTGCTGGTGCGACTGCCAAACAGCAAACCGCTTCTCCTGACG 600
ATCGATGCTGCCTACACCCTGGACCACTGGGAGGAGAAGGCTTTGCCTGGCTTCCTCGCC 660
TCGACCGTTGACACGGTCCGTTCGGTTCAGAAACTCCGAACCTATGCCGAAAAGCATGAT 720
GCGACGGTCGTTACCGGCCATGACCCTGACGCGTGGGCGAACTTCAAGAAGGCTCCCGAA 780
TTTTACGCGTAAATAAAACGCGCAAGTCAACAGCCAGATGCGGCGAGGTTGCGTGCAGCC 840
stop TCGCCGATTTTTGTCATATGAGCCAAGGACCCCGAACCTGGCGGGACCGTGTATTTCTGC 900
GCAGAGGCCTTTTCAGGATATACGCCTTCACTCAGGTCGTTCGCGTTGTCGCCTCAAGGC 960
CTGAAAGCTGTCCTCCCGCTGCGCGAGTGTCCCCATATGCGGTTTATTACCCCGGCGTTA 1020
CTGTGGGCCATCAGGCTTCGGGCTGACAATTTGCAAATGCCGGATGGCTTAAAGTAGACT 1080
TGTCTCTTTGATCCAAGCCGTCGGCAAATGGTGCAGATTGTGGCGCCTATTTTGCGTTCC 1140
CAAGGCGTCGGGCCAGCCATGCCCCCCAAAACAGGCTTGCGAAAAACCGAAGCGGCTCGT 1200
TGAAACCCGCGCCGGCCAGCAATGAAACGACCTCGTCTTCCGATCGGGGTGGCTCTGCAC 1260
CCTGCAG 1267
PstI

FIG. 4A

VTDIRLYMLQSGTLKCKVHNIKMNQGNGADYEIPVPFFLI 40
THPGGHTVIDGGNAIEVATDPRGHWGGICDVYWPVLDKDQ 80
GCVDQIKALGFDPADVKYVVQSHLHLDHTGAIGRFPNATH 120
IVQRSEYEYAFTPDWFAGGGYIRKDFDKPGLKWQFLNGTQ 160
DDYYDVYGDGTLTTIFTPGHAPGHQSLLVRLPNSKPLLLT 200
IDAAYTLDHWEEKALPGFLASTVDTVRSVQKLRTYAEKHD 240
ATVVTGHDPDAWANFKKAPEFYA. 263

FIG. 4B

```
AiiB : 1                                                               VTDIRLY 7

AttM                                                                   -------

AiiB : 8   MLQSGTLKCKVHNIKMNQGNGADYEIPVPFFLITHPGGHTVIDGGNAIEVATDPRGHWGG 67
           MLQSGTLKCKVHNIKMNQGNGADYEIPVPFFLITHP GHTVIDGGNAIEVATDPRGHWGG
AttM : 1   MLQSGTLKCKVHNIKMNQGNGADYEIPVPFFLITHPAGHTVIDGGNAIEVATDPRGHWGG 60

AiiB : 68  ICDVYWPVLDKDQGCVDQIKALGFDPADVKYVVQSHLHLDHTGAIGRFPNATHIVQRSEY 127
           ICDVYWPVLDKDQGCVDQIKALGFDPADVKYVVQSHLHLDHTGAIGRFPNATHIVQRSEY
AttM : 61  ICDVYWPVLDKDQGCVDQIKALGFDPADVKYVVQSHLHLDHTGAIGRFPNATHIVQRSEY 120

AiiB : 128 EYAFTPDWFAGGGYIRKDFDKPGLKWQFLNGTQDDYYDVYGDGTLTTIFTPGHAPGHQSL 187
           EYAFTPDWFAGGGYIRKDFDKPGLKWQFLNG QDDYYDVYGDGTLTTIFTPGHAPGHQS
AttM : 121 EYAFTPDWFAGGGYIRKDFDKPGLKWQFLNGAQDDYYDVYGDGTLTTIFTPGHAPGHQSF 180

AiiB : 188 LVRLPNSKPLLLTIDAAYTLDHWEEKALPGFLASTVDTVRSVQKLRTYAEKHDATVVTGH 247
           LVRLPNSKPLLLTIDAAYTLDHWEEKALPGFLASTVDTVRSVQKLRTYAEKHDATVVTGH
AttM : 181 LVRLPNSKPLLLTIDAAYTLDHWEEKALPGFLASTVDTVRSVQKLRTYAEKHDATVVTGH 240

AiiB : 248 DPDAWANFKKAPEFYA 263
           DPDAWANFKKAPEFYA
AttM : 241 DPDAWANFKKAPEFYA 256
```

FIG. 5

```
          .T...LY....G...C.......N......  CONSENSUS

  1   VTDIRLYMLQSGTLKCKVHNIKMNQGNGAD       AiiB PROTEIN.PRO
  1   MTVKKLYFVPAG--RCMLDHSSVNSTLTPG       AiiA PROTEIN.PRO

          .....P....L.....G....D.G...E.A   CONSENSUS

 31   YEIPVPF--FLITHPGGHTVIDGGNAIEVA       AiiB PROTEIN.PRO
 29   ELLDLPVWCYLLETEEGPILVDTGMP-ESA       AiiA PROTEIN.PRO

          ....G...G......V..P........V..   CONSENSUS

 59   TDPRGHWGGI---CDVYWPVLDKDQGCVDQ       AiiB PROTEIN.PRO
 58   VNNEGLFNGTFVEGQVL-PKMTEEDRIVNI       AiiA PROTEIN.PRO

          .K..G..P.D..Y...SHLH.DH.G..G.F   CONSENSUS

 86   IKALGFDPADVKYVVQSHLHLDHTGAIGRF       AiiB PROTEIN.PRO
 87   LKRVGYEPEDLLYIISSHLHFDHAGGNGAF       AiiA PROTEIN.PRO

          .N...IVQR.EYE............Y..K.  CONSENSUS

116   PNATHIVQRSEYEYAFTPDWFAGGGYIRKD       AiiB PROTEIN.PRO
117   INTPIIVQRAEYE---AAQ--HSEEYL-KE       AiiA PROTEIN.PRO

          ...P.L......G.....Y.V.....L...  CONSENSUS

146   FDKPGLKWQFLNGTQDDYYDVYGDGTLTTI       AiiB PROTEIN.PRO
141   CILPNLNYKIIEGD----YEVVPGVQL--L       AiiA PROTEIN.PRO

          .TPGH.PGHQSLL.....S.P.LLTIDA.Y  CONSENSUS

176   FTPGHAPGHQSLLVRLPNSKPLLLTIDAAY       AiiB PROTEIN.PRO
165   HTPGHTPGHQSLLIETEKSGPVLLTIDASY       AiiA PROTEIN.PRO

          T....E......GF.........S...L..  CONSENSUS

206   TLDHWEEKA-LPGFLASTVDTVRSVQKLRT       AiiB PROTEIN.PRO
195   TKENFENEVPFAGFDSEL--ALSSIKRLKE       AiiA PROTEIN.PRO

          ...K....V..GHD.............PE   CONSENSUS

235   YAEKHDATVVTGHDPDAWANFKKA----PE       AiiB PROTEIN.PRO
223   VVMKEKPIVFFGHDIEQ----ERGCKVFPE       AiiA PROTEIN.PRO

          .Y.-                            CONSENSUS

261   FYA.                                 AiiB PROTEIN.PRO
249   -YI.                                 AiiA PROTEIN.PRO
```

FIG. 6 aiiC seq

```
gaattctttacttctatattatagatggtgaaatactgctatgtaaaaaaaataccctct    60
tttttctgtaagctgtactgatagtctagaaggagtttatttctaaaaagaagaattttt   120
tactgtattacttatcccaaactaaatgtaaaggtggatacataATGACAGTAAAGAAG   180
CTTTATTTCGTTCCAGCAGGTCGTTGTATGTTAGATCATTCTTCTGTTAATAGTACAATC   240
GCGCCGGGAAATTTATTGAACTTACCTGTATGGTGTTATCTTTTGGAGACGGAAGAAGGT   300
CCCATTTTAGTAGATACAGGTATGCCAGAAAGTGCGGTTAATAATGAAAACTTGTTTGAA   360
GGGACATTTGCAGAAGGACAGATTTTACCGAAAATGACTGAAGAAGATAGAATAATAGCT   420
ATTTTAAAACGTGCAGGGTATGAGCCAGATGACCTCCTATATATTATTAGTTCACATTTG   480
CATTTTGATCATGCAGGAGGAAATGGTGCTTTTATTAATACTCCAATCATTATACAGCGT   540
GCTGAATATGAGGCAGCGCAGTATAGAGAGGAATATTTGAAAGAGTGTATACTGCCGAAT   600
TTGAACTACAAAATTATTGAAGGGGATTATGAAGTGGTACCAGGTGTTCAACTATTGTAT   660
ACACCAGGACATTCACCAGGGCATCAGTCACTATTAATTGAGACAGAAAAATCTGGTGTT   720
GTGTTATTAACCATTGATGCATCTTATACGAAAGAGAATTTTGAAGATGAAGTACCGTTT   780
GCTGGATTTGATCCAGAATTAGCTTTATCATCAATTAAACGTTTAAAAGAAGTTGTGATG   840
AAAGAGAAGCCGCTTGTTTTCTTTGGACATGATATAGAGCAGGAAAAGGGATGTAAAGTG   900
TTCCCGGAATATATATAGtgcaaaaagtcatgagcttacgtgctcatgactttttgattt   960
aaataatttttttaaataagttataaacttttttggaactatcttcatttaattgatagt  1020
acgtaagatttacatcatcaggagtatcttgctgtgcaatcatcacttcgttactatgat  1080
gatcaactacccatatgaaatatttttataagtaccatcctcaaatgtaatccacatat  1140
cacaatctattaaatctgatccttcttcatctaatgttaattttccttttttggccgtat  1200
tcatactgttaatgaatgtctttaattcatctgttttgcgagaaagatatcttttttg   1260
ttttaatggactcgacatgtatatcttttatttcctgttttcccaaaaagacagggggct  1320
catttggatcccttgagt                                            1339
```

FIG. 8A aiiC seq

```
MTVKKLYFVPAGRCMLDHSSVNSTIAPGNLLNLPVWCYLLETEEGPILVDTGMPESAVNN    60
ENLFEGTFAEGQILPKMTEEDRIIAILKRAGYEPDDLLYIISSHLHFDHAGGNGAFINTP   120
IIIQRAEYEAAQYREEYLKECILPNLNYKIIEGDYEVVPGVQLLYTPGHSPGHQSLLIET   180
EKSGVVLLTIDASYTKENFEDEVPFAGFDPELALSSIKRLKEVVMKEKPLVFFGHDIEQE   240
KGCKVFPEYI                                                    250
```

FIG. 8B aiiD

ATGACAGTAAAGAAGCTTTATTTCATCCCAGCAGGTCGTTGCATGTTGGATCATTCGTCTGTTAACAGTGCGTTAACACC
GGGGAAACTATTAAACTTGCCGGTGTGGTGTTATCTTTTGGAGACGGAAGAAGGTCCTATTTTAGTAGACACAGGTATGC
CAGAAAGTGCAGTTAATAATGAAGGGCTTTTTAACGGTACATTTGTTGAAGGACAGATCTTACCGAAAATGACTGAAGAA
GATAGAATCGTGAATATATTAAAGCGTGTGGGGTATGAGCCGGACGACCTTTTATATATTATTAGTTCTCACTTACATTT
TGATCATGCAGGAGGAAACGGTGCTTTTACAAATACACCAATTATTGTGCAGCGAACGGAATATGAGGCAGCACTTCATA
GAGAAGAATATATGAAAGAATGTATATTACCGCATTTGAACTACAAAATTATTGAAGGGGATTATGAAGTGGTACCAGGT
GTTCAATTATTGTATACGCCAGGTCATTCTCCAGGCCATCAGTCGCTATTCATTGAGACGGAGCAATCCGGTTCAGTTTT
ATTAATGATTGATGCATCGTACACGAAAGAGAATTTTGAAGATGAAGTGCCGTTCGCAGGATTTGATCCAGAATTAGCTT
TATCTTCAATTAAACGTTTAAAAGAAGTTGTGAAAAAAGAGAAACCAATTATTTTCTTTGGTCATGATACAGAGCAGGAA
AAGAGTTGTAGAGTGTTCCCGGAATATATATAG

MTVKKLYFIPAGRCMLDHSSVNSALTPGKLLNLPVWCYLLETEEGPILVDTGMPESAVNNEGLFNGTFVEGQILPKMTEE
DRIVNILKRVGYEPDDLLYIISSHLHFDHAGGNGAFTNTPIIVQRTEYEAALHREEYMKECILPHLNYKIIEGDYEVVPG
VQLLYTPGHSPGHQSLFIETEQSGSVLLMIDASYTKENFEDEVPFAGFDPELALSSIKRLKEVVKKEKPIIFFGHDTEQE
KSCRVFPEYI

FIG. 9A aiiE

ATGACAGTAAAGAAGCTTTATTTCATCCCAGCAGGTCGTTGCATGTTGGATCATTCGTCTGTTAACAGTGCGTTAACACC
GGGGAAACTATTAAACTTGCCGGTGTGGTGTTATCTTTTGGAGACGGAAGAAGGTCCTATTTTAGTAGACACAGGTATGC
CAGAAAGTGCAGTTAATAATGAAGGGCTTTTTAACGGTACATTTGTTGAAGGACAGATCTTACCGAAAATGACTGAAGAA
GATAGAATCGTGAATATATTAAAGCGTGTAGGGTATGAGCCGGACGACCTTTTATATATTATTAGTTCTCACTTACATTT
TGATCATGCAGGAGGAAACGGTGCTTTTACAAATACACCAATTATTGTGCAGCGAACGGAATATGAGGCAGCACTTCATA
GAGAAGAATATATGAAAGAATGTATATTACCGCATTTGAACTACAAAATTATTGAAGGGGATTATGAAGTGGTACCAGGT
GTTCAATTATTGTATACGCCAGGTCATTCTCCAGGCCATCAGTCGCTATTCATTGAGACGGAGCAATCCGGTTCAGTTTT
ATTAACGATTGATGCATCGTACACGAAAGAGAATTTTGAAGATGAAGTGCCGTTCGCAGGATTTGATCCAGAATTAGCTT
TATCTTCAATTAAACGTTTAAAAGAAGTTGTGAAAAAAGAGAAACCAATTATTTTCTTTGGTCATGATATAGAGCAGGAA
AAGAGTTGTAGAGTGTTCCCGGAATATATATAG

MTVKKLYFIPAGRCMLDHSSVNSALTPGKLLNLPVWCYLLETEEGPILVDTGMPESAVNNEGLFNGTFVEGQILPKMTEE
DRIVNILKRVGYEPDDLLYIISSHLHFDHAGGNGAFTNTPIIVQRTEYEAALHREEYMKECILPHLNYKIIEGDYEVVPG
VQLLYTPGHSPGHQSLFIETEQSGSVLLTIDASYTKENFEDEVPFAGFDPELALSSIKRLKEVVKKEKPIIFFGHDIEQE
KSCRVFPEYI

FIG. 9B aiiF

ATGACAGTAAAGAAGCTTTATTTCGTCCCAGCAGGTCGTTGTATGTTAGATCATTCTTCTGTTAATAGTACACTCGCGCC
GGGGAATTTATTGAACTTACCTGTATGGTGTTATCTTTTGGAGACAGAAGAGGGGCCTATTTTAGTAGATACAGGTATGC
CAGAAAGTGCAGTTAATAATGAAGGGCTTtTTAACGGTACATTTGTTGAAGGACAGATTTTACCGAAAATGACTGAAGAA
GATAGAATCGTGAATATATTAAAGCGTGTAGGGTATGAGCCGGACGACCTTTTATATATTATTAGTTCTCACTTACATTT
TGATCATGCAGGAGGAAACGGTGCTTTTACAAATACACCGATTATTGTGCAACGAACGGAATATGAGGCAGCACTTCATA
GAGAAGAATATATGAAAGAATGTATATTACCGCATTTGAACTATAAAATTATTGAAGGGGATTATGAAGTGGTACCAGGT
GTTCAATTATTGTATACGCCAGGTCATTCTCCAGGCCATCAGTCGCTATTAATTGAGACAGAAAAATCCGGTCTTGTATT
ATTAACGATTGATGCATCTTATACGAAAGAAAATTTTGAAGATGAAGTGCCGTTCGCGGGATTTGATTCGGAATTAGCTT
TATCTTCAATTAAACGTTTAAAAGAAGTTGTGATGAAAGAGAAGCCAATTATTTTCTTTGGTCATGATATAGAACAGGAA
AAGGGATTTAAAGTGTTCCCTGAATATATATAA

MTVKKLYFVPAGRCMLDHSSVNSTLAPGNLLNLPVWCYLLETEEGPILVDTGMPESAVNNEGLFNGTFVEGQILPKMTEE
DRIVNILKRVGYEPDDLLYIISSHLHFDHAGGNGAFTNTPIIVQRTEYEAALHREEYMKECILPHLNYKIIEGDYEVVPG
VQLLYTPGHSPGHQSLLIETEKSGLVLLTIDASYTKENFEDEVPFAGFDSELALSSIKRLKEVVMKEKPIIFFGHDIEQE
KGFKVFPEYI

FIG. 9C aiiG

ATGACAGTAAAGAAGCTTTATTTCGTCCCAGCAGGTCGTTGTATGTTGGATCATTCGTCTGTTAACAGTGCGTTAACACC
GGGAAAACTATTAAACTTGCCGGTTTGGTGTTATCTTTTGGAGACGGAAGAAGGTCCTATTTTAGTAGACACAGGTATGC
CAGAAAGTGCAGTTAATAATGAAGGGCTTTTTAACGGTACATTTGCAAAAGGACAGATTTTACCGAAAATGACTGAAGAA
GATAGAATTGTAACTATTTTAAAACGTGCAGGGTATGAGCCAGATGATCTCCTATATATTATTAGTTCGCACTTGCATTT
TGATCATGCAGGAGGAAATGGTGCTTTTTTGAATACGCCAaTCATTATACAACGTGCTGAATATGAGGCAGCGCAGCATA
GAGAGGAATATTTGAAAGAGTGCATACTACCAGATTTAAACTACAAAATTATTGAAGGTGATTATGAAGTGGTACCTGGT
GTTCGGTTATTGTATACACCAGGACATTCTCCAGGGCATCAGTCATTATTAATTGAGACGGAAAAATCCGGTCCTGTATT
ATTAACGATTGATGCATCTTATACGAAAGAGAATTTTGAAGATGAAGTACCGTTTGCGGGATTTGATTCGGAATTAGCCT
TATCTTCAATTAAACGTTTAAAAGAAGTTGTGATGAAAGAGAAACCGATTGTTTTCTTTGGACATGATATAGAACAGGAA
AAGGGATGTAAAGTGTTCCCTGAATATATATAG

MTVKKLYFVPAGRCMLDHSSVNSALTPGKLLNLPVWCYLLETEEGPILVDTGMPESAVNNEGLFNGTFAKGQILPKMTEE
DRIVTILKRAGYEPDDLLYIISSHLHFDHAGGNGAFLNTPIIIQRAEYEAAQHREEYLKECILPDLNYKIIEGDYEVVPG
VRLLYTPGHSPGHQSLLIETEKSGPVLLTIDASYTKENFEDEVPFAGFDSELALSSIKRLKEVVMKEKPIVFFGHDIEQE
KGCKVFPEYI

FIG. 9D aiiH

ATGACAGTAAAGAAGCTTTATTTCATCCCAGCAGGTCGTTGTATGTTAGATCATTCTTCTGTTAATAGTACACTCGCGCC
GGGGAATTTATTGAACTTACCTGTATGGTGTTATCTTTTGGAGACAGAAGAAGGGCCTATTTTAGTAGATACAGGTATGC
CAGAAAGTGCAGTTAATAATGAAGGGCTTTTTAACGGTACATTTGTTGAAGGACAGATTTTACCGAAAATGACTGAAGAA
GATAGAATCGTGAATATATTAAAGCGTGTAGGGTATGAGCCGGACGACCTTTTATATATTATTAGTTCTCACTTACATTT
TGATCATGCAGGAGGAAACGGTGCTTTTACAAATACACCGATTATTGTGCAGCGAGCGGAATATGAGGCAGCACTTCATA
GAGAAGAATATATGAAAGAATGTATATTACCGCATTTGAACTACAAAATTATTGAAGGGGATTATGAAGTGGTACCAGGT
GTTCAATTATTGTATACGCCAGGTCATTCTCCAGGCCATCAGTCGTTATTCATTGAGACGGAGCAATCCGGTTCAGTTTT
ATTAACAATTGATGCATCGTACACGAAAGAGAATTTTGAAGATGAAGTGCCGTTCGCAGGATTTGATCCAGAATTAGCTT
TATCTTCAATCAAACGTTTAAAAGGAGTTGTGGCGGAAGAGAAACCAATTGTTTTCTTTGGTCATGATATAGAGCAGGAA
AAGGGTTGTAGAGTGTTCCCTGAGTATATATAG

MTVKKLYFIPAGRCMLDHSSVNSTLAPGNLLNLPVWCYLLETEEGPILVDTGMPESAVNNEGLFNGTFVEGQILPKMTEE
DRIVNILKRVGYEPDDLLYIISSHLHFDHAGGNGAFTNTPIIVQRAEYEAALHREEYMKECILPHLNYKIIEGDYEVVPG
VQLLYTPGHSPGHQSLFIETEQSGSVLLTIDASYTKENFEDEVPFAGFDPELALSSIKRLKGVVAEEKPIVFFGHDIEQE
KGCRVFPEYI

FIG. 9E aiiI

ATGACAGTAAAGAAGCTTTATTTCGTCCCAGCAGGTCGTTGTATGTTAGATCATTCTTCTGTTAATAGTACACTCGCGCC
GGGGAATTTATTGAACTTACCTGTATGGTGTTATCTTTTGGAGACAGAAGAGGGGCCTATTTTAGTAGATACAGGTATGC
CAGAAAGTGCAGTTAATAATGAAGGGCTTTTTAACGGTACATTTGTTGAAGGACAGATTTTACCGAAAATGACTGAAGAA
GATAGAATCGTGAATATATTAAAGCGTGTAGGGTATGAGCCGGACGACCTTTTATATATTATTAGTTCTCACTTACATTT
TGATCATGCAGGAGGAAACGGTGCTTTTACAAATACACCGATTATTGTGCAGCGAGCGGAATATGAGGCAGCACTTCATA
GAGAAGAATATATGAAAGAATGTATATTACCGCATTTGAACTACAAAATTATTGAAGGGGATTATGAAGTGGTACCAGGT
GTTCAATTATTGTATACGCCAGGTCATTCTCCAGGCCATCAGTCGTTATTCATTGAGACGGACAATTCCGGTTCAGTTTT
ATTAACAATTGATGCATCGTACACGAAAGAGAATTTTGAAGATGAAGTGCCGTTCGCAGGATTTGATCCAGAATTAGCTT
TATCTTCAATCAAACGTTTAAAAGGAGTTGTGGCGGAAGAGAAACCAATTGTTTTCTTTGGTCATGATATAGAGCAGGAA
AAGGGTTGTAGAGTGTTCCCTGAGTATATATAG

MTVKKLYFVPAGRCMLDHSSVNSTLAPGNLLNLPVWCYLLETEEGPILVDTGMPESAVNNEGLFNGTFVEGQILPKMTEE
DRIVNILKRVGYEPDDLLYIISSHLHFDHAGGNGAFTNTPIIVQRAEYEAALHREEYMKECILPHLNYKIIEGDYEVVPG
VQLLYTPGHSPGHQSLFIETDNSGSVLLTIDASYTKENFEDEVPFAGFDPELALSSIKRLKGVVAEEKPIVFFGHDIEQE
KGCRVFPEYI

FIG. 9F aiiJ

ATGACAGTAAAGAAGCTTTATTTCATCCCAGCAGGTCGTTGTATGTTAGATCATTCTTCTGTTAATAGTACACTCGCGCC
GGGGAATTTATTGAACTTACCTGTATGGTGTTATCTTTTGGAGACAGAAGAGGGGCCTATTTTAGTAGATACAGGTATGC
CAGAAAGTGCAGTTAATAATGAAGGGCTTTTTAACGGTACATTTGTTGAAGGACAGATTTTACCGAAAATGACTGAAGAA
GATAGAATCGTGAATATATTAAAGCGTGTAGGGTATGAGCCGGACGACCTTTTATATATTATTAGTTCTCACTTACATTT
TGATCATGCAGGAGGAAACGGTGCTTTTACAAATACACCGATTATTGTGCAGCGAGCGGAATATGAGGCAGCACTTCATA
GAGAAGAATATATGAAAGAATGTATATTACCGCATTTGAACTACAAAATTATTGAAGGGGATTATGAAGTGGTACCAGGT
GTTCAATTATTGTATACGCCAGGTCATTCTCCAGGCCATCAGTCGTTATTCATTGAGACGGAGCAATCCGGTTCAGTTTT
ATTAACAATTGATGCATCGTACACGAAAGAGAATTTTGAAGATGAAGTGCCGTTCGCAGGATTTGATCCAGAATTAGCTT
TATCTTCAATCAAACGTTTAAAAGGAGTTGTGGCGGAAGAGAAACCAATTGTTTTCTTTGGTCATGATATAGAGCAGGAA
AAGGGTTGTAGAGTGTTCCCTGAGTATATATAG

MTVKKLYFIPAGRCMLDHSSVNSTLAPGNLLNLPVWCYLLETEEGPILVDTGMPESAVNNEGLFNGTFVEGQILPKMTEE
DRIVNILKRVGYEPDDLLYIISSHLHFDHAGGNGAFTNTPIIVQRAEYEAALHREEYMKECILPHLNYKIIEGDYEVVPG
VQLLYTPGHSPGHQSLFIETEQSGSVLLTIDASYTKENFEDEVPFAGFDPELALSSIKRLKGVVAEEKPIVFFGHDIEQE
KGCRVFPEYI

FIG. 9G aiiK

ATGACAGTAAAGAAGCTTTATTTCATCCCAGCAGGTCGTTGTATGTTAGATCATTCTTCTGTTAATGGTACACTCGCGCC
GGGGAATTTATTGAACTTACCTGTATGGTGTTATCTTTTGGAGACAGAAGAAGGGGCCATTTTAGTAGATACAGGTATGC
CAGAAAGTGCAGTTAATAATGAAGGGCTTTTTAACGGTACATTTGTTGAAGGACAGATTTTACCGAAAATGACTGAAGAA
GATAGAATCGTGAATATATTAAAGCGTGTAGGGTATGAGCCGGACGACCTTTTATATATTATTAGTTCTCACTTACATTT
TGATCATGCAGGAGGAAACGGTGCTTTTACAAATACACCGATTATTGTGCAGCGAACGGAATATGAGGCAGCACTTCATA
GAGAAGAATATATGAAAGAATGTATATTACCGCATTTGAACTACAAAATTATTGAAGGGGATTATGAAGTGGTaCCAGGT
GTTCAATTATTGTATACGCCAGGTCATTCTCCAGGCCATCAGTCGTTATTCATTGAGACGGAGCAATCCGGTTCAGTTTT
ATTAACAATTGATGCATCGTACACGAAAGAGAATTTTGAAGATGAAGTGCCGTTCGCAGGATTTGATCCAGAATTAGCTT
TATCTTCAATTAAACGTTTAAAAGGAGTTGTGGCGAAAGAGAAACCAATTGTTTTCTTTGGTCATGATATAGAGCAGGAA
AAGGGTTGTAGAGTGTTCCCTGAGTaTATATAG

MTVKKLYFIPAGRCMLDHSSVNGTLAPGNLLNLPVWCYLLETEEGAILVDTGMPESAVNNEGLFNGTFVEGQILPKMTEE
DRIVNILKRVGYEPDDLLYIISSHLHFDHAGGNGAFTNTPIIVQRTEYEAALHREEYMKECILPHLNYKIIEGDYEVVPG
VQLLYTPGHSPGHQSLFIETEQSGSVLLTIDASYTKENFEDEVPFAGFDPELALSSIKRLKGVVAKEKPIVFFGHDIEQE
KGCRVFPEYI

FIG. 9H

SEQUENCE LISTING

```
<160> NUMBER OF SEQ ID NOS: 22

<210> SEQ ID NO 1
<211> LENGTH: 1581
<212> TYPE: DNA
<213> ORGANISM: Agrobacterium tumefaciens M103
<220> FEATURE:
<221> NAME/KEY: misc_feature
<222> LOCATION: (315)..(1103)
<223> OTHER INFORMATION: Coding sequence

<400> SEQUENCE: 1

ctgcagcgtc gctttatgcg gagcttgccg acgtgctggg tgttccgggt gaaggggatg     60

cggcaacccg ttcggatgcg ttcgttcagc atatggaaac gctgatggac gaaagcggcg    120

cgccgcgacg tctgcgcgat gtcggcgtga cggacaacac gctcgccatg cttgcgtccg    180

acgcaatgaa acagagccgt ctgttggtca ataatccggt cgaagtccgc gaagaggatg    240

cgcttgcgct ctaccgcgag gcgttctgac ccatttctga cagcaatatc ttcagtccca    300

agggaggaaa acgagtgacc gatatcagac tttacatgct tcagtcgggt acgctgaaat    360

gcaaggtaca caacatcaag atgaaccagg ggaacggtgc agactatgag atccccgttc    420

cgtttttcct gattacccat ccgggcgggc acaccgtgat cgacggcggc aacgcgattg    480

aagttgcaac ggatccgcgt ggccattggg gcggcatctg cgatgtctat tggccagtgc    540

tggacaagga ccagggctgc gttgaccaga tcaaggcgct tggtttcgat ccggccgatg    600

tcaagtatgt tgtgcagtcg cacctgcatc tcgatcatac cggcgccatc ggtcgcttcc    660

ccaacgcaac ccacatcgtg cagcgctcgg aatatgagta tgccttcacg cccgactggt    720

ttgccggtgg cggctatatc cgcaaggact tcgacaagcc gggcctgaag tggcagttcc    780

tcaacggtac gcaggacgac tattacgacg tttacggcga cggcacgctc accacgatct    840

tcacgcccgg tcatgcgccc ggccaccagt ccttgctggt gcgactgcca aacagcaaac    900

cgcttctcct gacgatcgat gctgcctaca ccctggacca ctgggaggag aaggctttgc    960

ctggcttcct cgcctcgacc gttgacacgg tccgttcggt tcagaaactc cgaacctatg   1020

ccgaaaagca tgatgcgacg gtcgttaccg gccatgaccc tgacgcgtgg gcgaacttca   1080

agaaggctcc cgaattttac gcgtaaataa aacgcgcaag tcaacagcca gatgcggcga   1140

ggttgcgtgc agcctcgccg atttttgtca tatgagccaa ggaccccgaa cctggcggga   1200

ccgtgtattt ctgcgcagag gccttttcag gatatacgcc ttcactcagg tcgttcgcgt   1260

tgtcgcctca aggcctgaaa gctgtcctcc cgctgcgcga gtgtccccat atgcggttta   1320
```

-continued

```
ttaccccggc gttactgtgg gccatcaggc ttcgggctga caatttgcaa atgccggatg   1380

gcttaaagta gacttgtctc tttgatccaa gccgtcggca aatggtgcag attgtggcgc   1440

ctattttgcg ttcccaaggc gtcgggccag ccatgccccc caaaacaggc ttgcgaaaaa   1500

ccgaagcggc tcgttgaaac ccgcgccggc cagcaatgaa acgacctcgt cttccgatcg   1560

gggtggctct gcaccctgca g                                             1581
```

<210> SEQ ID NO 2
<211> LENGTH: 1339
<212> TYPE: DNA
<213> ORGANISM: Bacillus thuringiensis Cot1
<220> FEATURE:
<221> NAME/KEY: misc_feature
<222> LOCATION: (166)..(918)
<223> OTHER INFORMATION: Coding sequence

<400> SEQUENCE: 2

```
gaattcttta cttctatatt atagatggtg aaatactgct atgtaaaaaa aataccctct     60

tttttctgta agctgtactg atagtctaga aggagtttat ttctaaaaag aagaattttt    120

tactgtatta ctttatccca aactaaatgt aaaggtggat acataatgac agtaaagaag    180

ctttatttcg ttccagcagg tcgttgtatg ttagatcatt cttctgttaa tagtacaatc    240

gcgccgggaa atttattgaa cttacctgta tggtgttatc ttttggagac ggaagaaggt    300

cccattttag tagatacagg tatgccagaa agtgcggtta ataatgaaaa cttgtttgaa    360

gggacatttg cagaaggaca gattttaccg aaaatgactg aagaagatag aataatagct    420

attttaaaac gtgcagggta tgagccagat gacctcctat atattattag ttcacatttg    480

cattttgatc atgcaggagg aaatggtgct tttattaata ctccaatcat tatacagcgt    540

gctgaatatg aggcagcgca gtatagagag gaatatttga aagagtgtat actgccgaat    600

ttgaactaca aaattattga aggggattat gaagtggtac caggtgttca actattgtat    660

acaccaggac attcaccagg gcatcagtca ctattaattg agacagaaaa atctggtgtt    720

gtgttattaa ccattgatgc atcttatacg aaagagaatt ttgaagatga agtaccgttt    780

gctggatttg atccagaatt agctttatca tcaattaaac gtttaaaaga agttgtgatg    840

aaagagaagc cgcttgtttt ctttggacat gatatagagc aggaaaaggg atgtaaagtg    900

ttcccggaat atatatagtg caaaaagtca tgagcttacg tgctcatgac tttttgattt    960

aaataatttt tttaaataag ttataaactt ttttggaact atcttcattt aattgatagt   1020

acgtaagatt tacatcatca ggagtatctt gctgtgcaat catcacttcg ttactatgat   1080

gatcaactac ccatatgaaa tattttttat aagtaccatc ctcaaatgta atccacatat   1140

cacaatctat taaatctgat ccttcttcat ctaatgttaa ttttcctttt ttggccgtat   1200

tcatactgtt aatgaatgtc tttaattcat ctgtttttgc gagaaagata tctttttttg   1260

ttttaatgga ctcgacatgt atatctttta tttcctgttt tcccaaaaag acagggggct   1320

catttggatc cctttgagt                                                1339
```

<210> SEQ ID NO 3
<211> LENGTH: 753
<212> TYPE: DNA
<213> ORGANISM: Bacillus thuringiensis B1

<400> SEQUENCE: 3

```
atgacagtaa agaagcttta tttcatccca gcaggtcgtt gcatgttgga tcattcgtct     60

gttaacagtg cgttaacacc ggggaaacta ttaaacttgc cggtgtggtg ttatcttttg    120
```

-continued gagacggaag aaggtcctat tttagtagac acaggtatgc cagaaagtgc agttaataat 180
gaagggcttt ttaacggtac atttgttgaa ggacagatct taccgaaaat gactgaagaa 240
gatagaatcg tgaatatatt aaagcgtgtg ggtatgagc cggacgacct tttatatatt 300
attagttctc acttacattt tgatcatgca ggaggaaacg gtgcttttac aaatacacca 360
attattgtgc agcgaacgga atatgaggca gcacttcata gagaagaata tatgaaagaa 420
tgtatattac cgcatttgaa ctacaaaatt attgaagggg attatgaagt ggtaccaggt 480
gttcaattat tgtatacgcc aggtcattct ccaggccatc agtcgctatt cattgagacg 540
gagcaatccg gttcagtttt attaatgatt gatgcatcgt acacgaaaga gaattttgaa 600
gatgaagtgc cgttcgcagg atttgatcca gaattagctt tatcttcaat taaacgttta 660
aaagaagttg tgaaaaaaga gaaaccaatt attttctttg gtcatgatac agagcaggaa 720
aagagttgta gagtgttccc ggaatatata tag 753

<210> SEQ ID NO 4
<211> LENGTH: 753
<212> TYPE: DNA
<213> ORGANISM: Bacillus thuringiensis B2

<400> SEQUENCE: 4
atgacagtaa agaagcttta tttcatccca gcaggtcgtt gcatgttgga tcattcgtct 60
gttaacagtg cgttaacacc ggggaaacta ttaaacttgc cggtgtggtg ttatcttttg 120
gagacggaag aaggtcctat tttagtagac acaggtatgc cagaaagtgc agttaataat 180
gaagggcttt ttaacggtac atttgttgaa ggacagatct taccgaaaat gactgaagaa 240
gatagaatcg tgaatatatt aaagcgtgta gggtatgagc cggacgacct tttatatatt 300
attagttctc acttacattt tgatcatgca ggaggaaacg gtgcttttac aaatacacca 360
attattgtgc agcgaacgga atatgaggca gcacttcata gagaagaata tatgaaagaa 420
tgtatattac cgcatttgaa ctacaaaatt attgaagggg attatgaagt ggtaccaggt 480
gttcaattat tgtatacgcc aggtcattct ccaggccatc agtcgctatt cattgagacg 540
gagcaatccg gttcagtttt attaacgatt gatgcatcgt acacgaaaga gaattttgaa 600
gatgaagtgc cgttcgcagg atttgatcca gaattagctt tatcttcaat taaacgttta 660
aaagaagttg tgaaaaaaga gaaaccaatt attttctttg gtcatgatat agagcaggaa 720
aagagttgta gagtgttccc ggaatatata tag 753

<210> SEQ ID NO 5
<211> LENGTH: 753
<212> TYPE: DNA
<213> ORGANISM: Bacillus thuringiensis B17

<400> SEQUENCE: 5
atgacagtaa agaagcttta tttcgtccca gcaggtcgtt gtatgttaga tcattcttct 60
gttaatagta cactcgcgcc ggggaattta ttgaacttac ctgtatggtg ttatcttttg 120
gagacagaag aggggcctat tttagtagat acaggtatgc cagaaagtgc agttaataat 180
gaagggcttt ttaacggtac atttgttgaa ggacagattt taccgaaaat gactgaagaa 240
gatagaatcg tgaatatatt aaagcgtgta gggtatgagc cggacgacct tttatatatt 300
attagttctc acttacattt tgatcatgca ggaggaaacg gtgcttttac aaatacaccg 360
attattgtgc aacgaacgga atatgaggca gcacttcata gagaagaata tatgaaagaa 420

-continued tgtatattac cgcatttgaa ctataaaatt attgaagggg attatgaagt ggtaccaggt 480
gttcaattat tgtatacgcc aggtcattct ccaggccatc agtcgctatt aattgagaca 540
gaaaaatccg gtcttgtatt attaacgatt gatgcatctt atacgaaaga aaattttgaa 600
gatgaagtgc cgttcgcggg atttgattcg gaattagctt tatcttcaat taaacgttta 660
aaagaagttg tgatgaaaga gaagccaatt attttctttg gtcatgatat agaacaggaa 720
aagggattta aagtgttccc tgaatatata taa 753

<210> SEQ ID NO 6
<211> LENGTH: 753
<212> TYPE: DNA
<213> ORGANISM: Bacillus thuringiensis B18

<400> SEQUENCE: 6
atgacagtaa agaagcttta tttcgtccca gcaggtcgtt gtatgttgga tcattcgtct 60
gttaacagtg cgttaacacc gggaaaacta ttaaacttgc cggtttggtg ttatcttttg 120
gagacggaag aaggtcctat tttagtagac acaggtatgc cagaaagtgc agttaataat 180
gaagggcttt ttaacggtac atttgcaaaa ggacagattt taccgaaaat gactgaagaa 240
gatagaattg taactatttt aaaacgtgca gggtatgagc cagatgatct cctatatatt 300
attagttcgc acttgcattt tgatcatgca ggaggaaatg gtgctttttt gaatacgcca 360
atcattatac aacgtgctga atatgaggca gcgcagcata gagaggaata tttgaaagag 420
tgcatactac cagatttaaa ctacaaaatt attgaaggtg attatgaagt ggtacctggt 480
gttcggttat tgtatacacc aggacattct ccagggcatc agtcattatt aattgagacg 540
gaaaaatccg gtcctgtatt attaacgatt gatgcatctt atacgaaaga gaattttgaa 600
gatgaagtac cgtttgcggg atttgattcg gaattagcct tatcttcaat taaacgttta 660
aaagaagttg tgatgaaaga gaaaccgatt gttttctttg gacatgatat agaacaggaa 720
aagggatgta aagtgttccc tgaatatata tag 753

<210> SEQ ID NO 7
<211> LENGTH: 753
<212> TYPE: DNA
<213> ORGANISM: Bacillus thuringiensis B20

<400> SEQUENCE: 7
atgacagtaa agaagcttta tttcatccca gcaggtcgtt gtatgttaga tcattcttct 60
gttaatagta cactcgcgcc ggggaattta ttgaacttac ctgtatggtg ttatcttttg 120
gagacagaag aagggcctat tttagtagat acaggtatgc cagaaagtgc agttaataat 180
gaagggcttt ttaacggtac atttgttgaa ggacagattt taccgaaaat gactgaagaa 240
gatagaatcg tgaatatatt aaagcgtgta gggtatgagc cggacgacct tttatatatt 300
attagttctc acttacattt tgatcatgca ggaggaaacg gtgcttttac aaatacaccg 360
attattgtgc agcgagcgga atatgaggca gcacttcata gagaagaata tatgaaagaa 420
tgtatattac cgcatttgaa ctacaaaatt attgaagggg attatgaagt ggtaccaggt 480
gttcaattat tgtatacgcc aggtcattct ccaggccatc agtcgttatt cattgagacg 540
gagcaatccg gttcagtttt attaacaatt gatgcatcgt acacgaaaga gaattttgaa 600
gatgaagtgc cgttcgcagg atttgatcca gaattagctt tatcttcaat caaacgttta 660
aaaggagttg tggcggaaga gaaaccaatt gttttctttg gtcatgatat agagcaggaa 720
aagggttgta gagtgttccc tgagtatata tag 753

-continued

<210> SEQ ID NO 8
<211> LENGTH: 753
<212> TYPE: DNA
<213> ORGANISM: Bacillus thuringiensis B21

<400> SEQUENCE: 8

```
atgacagtaa agaagcttta tttcgtccca gcaggtcgtt gtatgttaga tcattcttct     60

gttaatagta cactcgcgcc ggggaattta ttgaacttac ctgtatggtg ttatcttttg    120

gagacagaag aggggcctat tttagtagat acaggtatgc cagaaagtgc agttaataat    180

gaagggcttt ttaacggtac atttgttgaa ggacagattt taccgaaaat gactgaagaa    240

gatagaatcg tgaatatatt aaagcgtgta gggtatgagc cggacgacct tttatatatt    300

attagttctc acttacattt tgatcatgca ggaggaaacg gtgcttttac aaatacaccg    360

attattgtgc agcgagcgga atatgaggca gcacttcata gagaagaata tatgaaagaa    420

tgtatattac cgcatttgaa ctacaaaatt attgaagggg attatgaagt ggtaccaggt    480

gttcaattat tgtatacgcc aggtcattct ccaggccatc agtcgttatt cattgagacg    540

gacaattccg gttcagtttt attaacaatt gatgcatcgt acacgaaaga gaattttgaa    600

gatgaagtgc cgttcgcagg atttgatcca gaattagctt tatcttcaat caaacgttta    660

aaaggagttg tggcggaaga gaaaccaatt gttttctttg gtcatgatat agagcaggaa    720

aagggttgta gagtgttccc tgagtatata tag                                 753
```

<210> SEQ ID NO 9
<211> LENGTH: 753
<212> TYPE: DNA
<213> ORGANISM: Bacillus thuringiensis B22

<400> SEQUENCE: 9

```
atgacagtaa agaagcttta tttcatccca gcaggtcgtt gtatgttaga tcattcttct     60

gttaatagta cactcgcgcc ggggaattta ttgaacttac ctgtatggtg ttatcttttg    120

gagacagaag aggggcctat tttagtagat acaggtatgc cagaaagtgc agttaataat    180

gaagggcttt ttaacggtac atttgttgaa ggacagattt taccgaaaat gactgaagaa    240

gatagaatcg tgaatatatt aaagcgtgta gggtatgagc cggacgacct tttatatatt    300

attagttctc acttacattt tgatcatgca ggaggaaacg gtgcttttac aaatacaccg    360

attattgtgc agcgagcgga atatgaggca gcacttcata gagaagaata tatgaaagaa    420

tgtatattac cgcatttgaa ctacaaaatt attgaagggg attatgaagt ggtaccaggt    480

gttcaattat tgtatacgcc aggtcattct ccaggccatc agtcgttatt cattgagacg    540

gagcaatccg gttcagtttt attaacaatt gatgcatcgt acacgaaaga gaattttgaa    600

gatgaagtgc cgttcgcagg atttgatcca gaattagctt tatcttcaat caaacgttta    660

aaaggagttg tggcggaaga gaaaccaatt gttttctttg gtcatgatat agagcaggaa    720

aagggttgta gagtgttccc tgagtatata tag                                 753
```

<210> SEQ ID NO 10
<211> LENGTH: 753
<212> TYPE: DNA
<213> ORGANISM: Bacillus thuringiensis B25

<400> SEQUENCE: 10

```
atgacagtaa agaagcttta tttcatccca gcaggtcgtt gtatgttaga tcattcttct     60
```

-continued

```
gttaatggta cactcgcgcc ggggaattta ttgaacttac ctgtatggtg ttatcttttg    120

gagacagaag aaggggccat tttagtagat acaggtatgc cagaaagtgc agttaataat    180

gaagggcttt ttaacggtac atttgttgaa ggacagattt taccgaaaat gactgaagaa    240

gatagaatcg tgaatatatt aaagcgtgta gggtatgagc cggacgacct tttatatatt    300

attagttctc acttacattt tgatcatgca ggaggaaacg gtgcttttac aaatacaccg    360

attattgtgc agcgaacgga atatgaggca gcacttcata gagaagaata tatgaaagaa    420

tgtatattac cgcatttgaa ctacaaaatt attgaagggg attatgaagt ggtaccaggt    480

gttcaattat tgtatacgcc aggtcattct ccaggccatc agtcgttatt cattgagacg    540

gagcaatccg gttcagtttt attaacaatt gatgcatcgt acacgaaaga gaattttgaa    600

gatgaagtgc cgttcgcagg atttgatcca gaattagctt tatcttcaat taaacgttta    660

aaaggagttg tggcgaaaga gaaaccaatt gttttctttg gtcatgatat agagcaggaa    720

aagggttgta gagtgttccc tgagtatata tag                                753
```

```
<210> SEQ ID NO 11
<211> LENGTH: 263
<212> TYPE: PRT
<213> ORGANISM: Agrobacterium tumefaciens M103

<400> SEQUENCE: 11

Val Thr Asp Ile Arg Leu Tyr Met Leu Gln Ser Gly Thr Leu Lys Cys
1               5                   10                  15

Lys Val His Asn Ile Lys Met Asn Gln Gly Asn Gly Ala Asp Tyr Glu
            20                  25                  30

Ile Pro Val Pro Phe Phe Leu Ile Thr His Pro Gly Gly His Thr Val
        35                  40                  45

Ile Asp Gly Gly Asn Ala Ile Glu Val Ala Thr Asp Pro Arg Gly His
    50                  55                  60

Trp Gly Gly Ile Cys Asp Val Tyr Trp Pro Val Leu Asp Lys Asp Gln
65                  70                  75                  80

Gly Cys Val Asp Gln Ile Lys Ala Leu Gly Phe Asp Pro Ala Asp Val
                85                  90                  95

Lys Tyr Val Val Gln Ser His Leu His Leu Asp His Thr Gly Ala Ile
            100                 105                 110

Gly Arg Phe Pro Asn Ala Thr His Ile Val Gln Arg Ser Glu Tyr Glu
        115                 120                 125

Tyr Ala Phe Thr Pro Asp Trp Phe Ala Gly Gly Gly Tyr Ile Arg Lys
    130                 135                 140

Asp Phe Asp Lys Pro Gly Leu Lys Trp Gln Phe Leu Asn Gly Thr Gln
145                 150                 155                 160

Asp Asp Tyr Tyr Asp Val Tyr Gly Asp Gly Thr Leu Thr Thr Ile Phe
                165                 170                 175

Thr Pro Gly His Ala Pro Gly His Gln Ser Leu Leu Val Arg Leu Pro
            180                 185                 190

Asn Ser Lys Pro Leu Leu Leu Thr Ile Asp Ala Ala Tyr Thr Leu Asp
        195                 200                 205

His Trp Glu Glu Lys Ala Leu Pro Gly Phe Leu Ala Ser Thr Val Asp
    210                 215                 220

Thr Val Arg Ser Val Gln Lys Leu Arg Thr Tyr Ala Glu Lys His Asp
225                 230                 235                 240

Ala Thr Val Val Thr Gly His Asp Pro Asp Ala Trp Ala Asn Phe Lys
                245                 250                 255
```

-continued

```
Lys Ala Pro Glu Phe Tyr Ala
            260


<210> SEQ ID NO 12
<211> LENGTH: 250
<212> TYPE: PRT
<213> ORGANISM: Bacillus thuringiensis Cot1

<400> SEQUENCE: 12

Met Thr Val Lys Lys Leu Tyr Phe Val Pro Ala Gly Arg Cys Met Leu
1               5                   10                  15

Asp His Ser Ser Val Asn Ser Thr Ile Ala Pro Gly Asn Leu Leu Asn
            20                  25                  30

Leu Pro Val Trp Cys Tyr Leu Leu Glu Thr Glu Glu Gly Pro Ile Leu
        35                  40                  45

Val Asp Thr Gly Met Pro Glu Ser Ala Val Asn Asn Glu Asn Leu Phe
    50                  55                  60

Glu Gly Thr Phe Ala Glu Gly Gln Ile Leu Pro Lys Met Thr Glu Glu
65                  70                  75                  80

Asp Arg Ile Ile Ala Ile Leu Lys Arg Ala Gly Tyr Glu Pro Asp Asp
                85                  90                  95

Leu Leu Tyr Ile Ile Ser Ser His Leu His Phe Asp His Ala Gly Gly
            100                 105                 110

Asn Gly Ala Phe Ile Asn Thr Pro Ile Ile Ile Gln Arg Ala Glu Tyr
        115                 120                 125

Glu Ala Ala Gln Tyr Arg Glu Glu Tyr Leu Lys Glu Cys Ile Leu Pro
    130                 135                 140

Asn Leu Asn Tyr Lys Ile Ile Glu Gly Asp Tyr Glu Val Val Pro Gly
145                 150                 155                 160

Val Gln Leu Leu Tyr Thr Pro Gly His Ser Pro Gly His Gln Ser Leu
                165                 170                 175

Leu Ile Glu Thr Glu Lys Ser Gly Val Val Leu Leu Thr Ile Asp Ala
            180                 185                 190

Ser Tyr Thr Lys Glu Asn Phe Glu Asp Glu Val Pro Phe Ala Gly Phe
        195                 200                 205

Asp Pro Glu Leu Ala Leu Ser Ser Ile Lys Arg Leu Lys Glu Val Val
    210                 215                 220

Met Lys Glu Lys Pro Leu Val Phe Phe Gly His Asp Ile Glu Gln Glu
225                 230                 235                 240

Lys Gly Cys Lys Val Phe Pro Glu Tyr Ile
                245                 250


<210> SEQ ID NO 13
<211> LENGTH: 250
<212> TYPE: PRT
<213> ORGANISM: Bacillus thuringiensis B1

<400> SEQUENCE: 13

Met Thr Val Lys Lys Leu Tyr Phe Ile Pro Ala Gly Arg Cys Met Leu
1               5                   10                  15

Asp His Ser Ser Val Asn Ser Ala Leu Thr Pro Gly Lys Leu Leu Asn
            20                  25                  30

Leu Pro Val Trp Cys Tyr Leu Leu Glu Thr Glu Glu Gly Pro Ile Leu
        35                  40                  45

Val Asp Thr Gly Met Pro Glu Ser Ala Val Asn Asn Glu Gly Leu Phe
    50                  55                  60
```

-continued

```
Asn Gly Thr Phe Val Glu Gly Gln Ile Leu Pro Lys Met Thr Glu Glu
65                  70                  75                  80

Asp Arg Ile Val Asn Ile Leu Lys Arg Val Gly Tyr Glu Pro Asp Asp
                85                  90                  95

Leu Leu Tyr Ile Ile Ser Ser His Leu His Phe Asp His Ala Gly Gly
            100                 105                 110

Asn Gly Ala Phe Thr Asn Thr Pro Ile Ile Val Gln Arg Thr Glu Tyr
        115                 120                 125

Glu Ala Ala Leu His Arg Glu Glu Tyr Met Lys Glu Cys Ile Leu Pro
    130                 135                 140

His Leu Asn Tyr Lys Ile Ile Glu Gly Asp Tyr Glu Val Val Pro Gly
145                 150                 155                 160

Val Gln Leu Leu Tyr Thr Pro Gly His Ser Pro Gly His Gln Ser Leu
                165                 170                 175

Phe Ile Glu Thr Glu Gln Ser Gly Ser Val Leu Leu Met Ile Asp Ala
            180                 185                 190

Ser Tyr Thr Lys Glu Asn Phe Glu Asp Glu Val Pro Phe Ala Gly Phe
        195                 200                 205

Asp Pro Glu Leu Ala Leu Ser Ser Ile Lys Arg Leu Lys Glu Val Val
    210                 215                 220

Lys Lys Glu Lys Pro Ile Ile Phe Phe Gly His Asp Thr Glu Gln Glu
225                 230                 235                 240

Lys Ser Cys Arg Val Phe Pro Glu Tyr Ile
                245                 250


<210> SEQ ID NO 14
<211> LENGTH: 250
<212> TYPE: PRT
<213> ORGANISM: Bacillus thuringiensis B2

<400> SEQUENCE: 14

Met Thr Val Lys Lys Leu Tyr Phe Ile Pro Ala Gly Arg Cys Met Leu
1               5                   10                  15

Asp His Ser Ser Val Asn Ser Ala Leu Thr Pro Gly Lys Leu Leu Asn
            20                  25                  30

Leu Pro Val Trp Cys Tyr Leu Leu Glu Thr Glu Glu Gly Pro Ile Leu
        35                  40                  45

Val Asp Thr Gly Met Pro Glu Ser Ala Val Asn Asn Glu Gly Leu Phe
    50                  55                  60

Asn Gly Thr Phe Val Glu Gly Gln Ile Leu Pro Lys Met Thr Glu Glu
65                  70                  75                  80

Asp Arg Ile Val Asn Ile Leu Lys Arg Val Gly Tyr Glu Pro Asp Asp
                85                  90                  95

Leu Leu Tyr Ile Ile Ser Ser His Leu His Phe Asp His Ala Gly Gly
            100                 105                 110

Asn Gly Ala Phe Thr Asn Thr Pro Ile Ile Val Gln Arg Thr Glu Tyr
        115                 120                 125

Glu Ala Ala Leu His Arg Glu Glu Tyr Met Lys Glu Cys Ile Leu Pro
    130                 135                 140

His Leu Asn Tyr Lys Ile Ile Glu Gly Asp Tyr Glu Val Val Pro Gly
145                 150                 155                 160

Val Gln Leu Leu Tyr Thr Pro Gly His Ser Pro Gly His Gln Ser Leu
                165                 170                 175

Phe Ile Glu Thr Glu Gln Ser Gly Ser Val Leu Leu Thr Ile Asp Ala
```

-continued

```
            180                 185                 190

Ser Tyr Thr Lys Glu Asn Phe Glu Asp Glu Val Pro Phe Ala Gly Phe
        195                 200                 205

Asp Pro Glu Leu Ala Leu Ser Ser Ile Lys Arg Leu Lys Glu Val Val
    210                 215                 220

Lys Lys Glu Lys Pro Ile Ile Phe Phe Gly His Asp Ile Glu Gln Glu
225                 230                 235                 240

Lys Ser Cys Arg Val Phe Pro Glu Tyr Ile
                245                 250


<210> SEQ ID NO 15
<211> LENGTH: 250
<212> TYPE: PRT
<213> ORGANISM: Bacillus thuringiensis B17

<400> SEQUENCE: 15

Met Thr Val Lys Lys Leu Tyr Phe Val Pro Ala Gly Arg Cys Met Leu
1               5                   10                  15

Asp His Ser Ser Val Asn Ser Thr Leu Ala Pro Gly Asn Leu Leu Asn
            20                  25                  30

Leu Pro Val Trp Cys Tyr Leu Leu Glu Thr Glu Glu Gly Pro Ile Leu
        35                  40                  45

Val Asp Thr Gly Met Pro Glu Ser Ala Val Asn Asn Glu Gly Leu Phe
    50                  55                  60

Asn Gly Thr Phe Val Glu Gly Gln Ile Leu Pro Lys Met Thr Glu Glu
65                  70                  75                  80

Asp Arg Ile Val Asn Ile Leu Lys Arg Val Gly Tyr Glu Pro Asp Asp
                85                  90                  95

Leu Leu Tyr Ile Ile Ser Ser His Leu His Phe Asp His Ala Gly Gly
            100                 105                 110

Asn Gly Ala Phe Thr Asn Thr Pro Ile Ile Val Gln Arg Thr Glu Tyr
        115                 120                 125

Glu Ala Ala Leu His Arg Glu Glu Tyr Met Lys Glu Cys Ile Leu Pro
    130                 135                 140

His Leu Asn Tyr Lys Ile Ile Glu Gly Asp Tyr Glu Val Val Pro Gly
145                 150                 155                 160

Val Gln Leu Leu Tyr Thr Pro Gly His Ser Pro Gly His Gln Ser Leu
                165                 170                 175

Leu Ile Glu Thr Glu Lys Ser Gly Leu Val Leu Leu Thr Ile Asp Ala
            180                 185                 190

Ser Tyr Thr Lys Glu Asn Phe Glu Asp Glu Val Pro Phe Ala Gly Phe
        195                 200                 205

Asp Ser Glu Leu Ala Leu Ser Ser Ile Lys Arg Leu Lys Glu Val Val
    210                 215                 220

Met Lys Glu Lys Pro Ile Ile Phe Phe Gly His Asp Ile Glu Gln Glu
225                 230                 235                 240

Lys Gly Phe Lys Val Phe Pro Glu Tyr Ile
                245                 250


<210> SEQ ID NO 16
<211> LENGTH: 250
<212> TYPE: PRT
<213> ORGANISM: Bacillus thuringiensis B18

<400> SEQUENCE: 16

Met Thr Val Lys Lys Leu Tyr Phe Val Pro Ala Gly Arg Cys Met Leu
```

-continued 1 5 10 15

Asp His Ser Ser Val Asn Ser Ala Leu Thr Pro Gly Lys Leu Leu Asn
20 25 30

Leu Pro Val Trp Cys Tyr Leu Leu Glu Thr Glu Glu Gly Pro Ile Leu
35 40 45

Val Asp Thr Gly Met Pro Glu Ser Ala Val Asn Asn Glu Gly Leu Phe
50 55 60

Asn Gly Thr Phe Ala Lys Gly Gln Ile Leu Pro Lys Met Thr Glu Glu
65 70 75 80

Asp Arg Ile Val Thr Ile Leu Lys Arg Ala Gly Tyr Glu Pro Asp Asp
85 90 95

Leu Leu Tyr Ile Ile Ser Ser His Leu His Phe Asp His Ala Gly Gly
100 105 110

Asn Gly Ala Phe Leu Asn Thr Pro Ile Ile Ile Gln Arg Ala Glu Tyr
115 120 125

Glu Ala Ala Gln His Arg Glu Glu Tyr Leu Lys Glu Cys Ile Leu Pro
130 135 140

Asp Leu Asn Tyr Lys Ile Ile Glu Gly Asp Tyr Glu Val Val Pro Gly
145 150 155 160

Val Arg Leu Leu Tyr Thr Pro Gly His Ser Pro Gly His Gln Ser Leu
165 170 175

Leu Ile Glu Thr Glu Lys Ser Gly Pro Val Leu Leu Thr Ile Asp Ala
180 185 190

Ser Tyr Thr Lys Glu Asn Phe Glu Asp Glu Val Pro Phe Ala Gly Phe
195 200 205

Asp Ser Glu Leu Ala Leu Ser Ser Ile Lys Arg Leu Lys Glu Val Val
210 215 220

Met Lys Glu Lys Pro Ile Val Phe Phe Gly His Asp Ile Glu Gln Glu
225 230 235 240

Lys Gly Cys Lys Val Phe Pro Glu Tyr Ile
245 250

<210> SEQ ID NO 17
<211> LENGTH: 250
<212> TYPE: PRT
<213> ORGANISM: Bacillus thuringiensis B20

<400> SEQUENCE: 17

Met Thr Val Lys Lys Leu Tyr Phe Ile Pro Ala Gly Arg Cys Met Leu
1 5 10 15

Asp His Ser Ser Val Asn Ser Thr Leu Ala Pro Gly Asn Leu Leu Asn
20 25 30

Leu Pro Val Trp Cys Tyr Leu Leu Glu Thr Glu Glu Gly Pro Ile Leu
35 40 45

Val Asp Thr Gly Met Pro Glu Ser Ala Val Asn Asn Glu Gly Leu Phe
50 55 60

Asn Gly Thr Phe Val Glu Gly Gln Ile Leu Pro Lys Met Thr Glu Glu
65 70 75 80

Asp Arg Ile Val Asn Ile Leu Lys Arg Val Gly Tyr Glu Pro Asp Asp
85 90 95

Leu Leu Tyr Ile Ile Ser Ser His Leu His Phe Asp His Ala Gly Gly
100 105 110

Asn Gly Ala Phe Thr Asn Thr Pro Ile Ile Val Gln Arg Ala Glu Tyr
115 120 125

-continued

```
Glu Ala Ala Leu His Arg Glu Glu Tyr Met Lys Glu Cys Ile Leu Pro
    130                 135                 140

His Leu Asn Tyr Lys Ile Ile Glu Gly Asp Tyr Glu Val Val Pro Gly
145                 150                 155                 160

Val Gln Leu Leu Tyr Thr Pro Gly His Ser Pro Gly His Gln Ser Leu
                165                 170                 175

Phe Ile Glu Thr Glu Gln Ser Gly Ser Val Leu Leu Thr Ile Asp Ala
            180                 185                 190

Ser Tyr Thr Lys Glu Asn Phe Glu Asp Glu Val Pro Phe Ala Gly Phe
        195                 200                 205

Asp Pro Glu Leu Ala Leu Ser Ser Ile Lys Arg Leu Lys Gly Val Val
    210                 215                 220

Ala Glu Glu Lys Pro Ile Val Phe Phe Gly His Asp Ile Glu Gln Glu
225                 230                 235                 240

Lys Gly Cys Arg Val Phe Pro Glu Tyr Ile
                245                 250


<210> SEQ ID NO 18
<211> LENGTH: 250
<212> TYPE: PRT
<213> ORGANISM: Bacillus thuringiensis B21

<400> SEQUENCE: 18

Met Thr Val Lys Lys Leu Tyr Phe Val Pro Ala Gly Arg Cys Met Leu
1               5                   10                  15

Asp His Ser Ser Val Asn Ser Thr Leu Ala Pro Gly Asn Leu Leu Asn
            20                  25                  30

Leu Pro Val Trp Cys Tyr Leu Leu Glu Thr Glu Glu Gly Pro Ile Leu
        35                  40                  45

Val Asp Thr Gly Met Pro Glu Ser Ala Val Asn Asn Glu Gly Leu Phe
    50                  55                  60

Asn Gly Thr Phe Val Glu Gly Gln Ile Leu Pro Lys Met Thr Glu Glu
65                  70                  75                  80

Asp Arg Ile Val Asn Ile Leu Lys Arg Val Gly Tyr Glu Pro Asp Asp
                85                  90                  95

Leu Leu Tyr Ile Ile Ser Ser His Leu His Phe Asp His Ala Gly Gly
            100                 105                 110

Asn Gly Ala Phe Thr Asn Thr Pro Ile Ile Val Gln Arg Ala Glu Tyr
        115                 120                 125

Glu Ala Ala Leu His Arg Glu Glu Tyr Met Lys Glu Cys Ile Leu Pro
    130                 135                 140

His Leu Asn Tyr Lys Ile Ile Glu Gly Asp Tyr Glu Val Val Pro Gly
145                 150                 155                 160

Val Gln Leu Leu Tyr Thr Pro Gly His Ser Pro Gly His Gln Ser Leu
                165                 170                 175

Phe Ile Glu Thr Asp Asn Ser Gly Ser Val Leu Leu Thr Ile Asp Ala
            180                 185                 190

Ser Tyr Thr Lys Glu Asn Phe Glu Asp Glu Val Pro Phe Ala Gly Phe
        195                 200                 205

Asp Pro Glu Leu Ala Leu Ser Ser Ile Lys Arg Leu Lys Gly Val Val
    210                 215                 220

Ala Glu Glu Lys Pro Ile Val Phe Phe Gly His Asp Ile Glu Gln Glu
225                 230                 235                 240

Lys Gly Cys Arg Val Phe Pro Glu Tyr Ile
                245                 250
```

-continued

<210> SEQ ID NO 19
<211> LENGTH: 250
<212> TYPE: PRT
<213> ORGANISM: Bacillus thuringiensis B22

<400> SEQUENCE: 19

```
Met Thr Val Lys Lys Leu Tyr Phe Ile Pro Ala Gly Arg Cys Met Leu
1               5                   10                  15

Asp His Ser Ser Val Asn Ser Thr Leu Ala Pro Gly Asn Leu Leu Asn
            20                  25                  30

Leu Pro Val Trp Cys Tyr Leu Leu Glu Thr Glu Glu Gly Pro Ile Leu
        35                  40                  45

Val Asp Thr Gly Met Pro Glu Ser Ala Val Asn Asn Glu Gly Leu Phe
    50                  55                  60

Asn Gly Thr Phe Val Glu Gly Gln Ile Leu Pro Lys Met Thr Glu Glu
65                  70                  75                  80

Asp Arg Ile Val Asn Ile Leu Lys Arg Val Gly Tyr Glu Pro Asp Asp
                85                  90                  95

Leu Leu Tyr Ile Ile Ser Ser His Leu His Phe Asp His Ala Gly Gly
            100                 105                 110

Asn Gly Ala Phe Thr Asn Thr Pro Ile Ile Val Gln Arg Ala Glu Tyr
        115                 120                 125

Glu Ala Ala Leu His Arg Glu Glu Tyr Met Lys Glu Cys Ile Leu Pro
    130                 135                 140

His Leu Asn Tyr Lys Ile Ile Glu Gly Asp Tyr Glu Val Val Pro Gly
145                 150                 155                 160

Val Gln Leu Leu Tyr Thr Pro Gly His Ser Pro Gly His Gln Ser Leu
                165                 170                 175

Phe Ile Glu Thr Glu Gln Ser Gly Ser Val Leu Leu Thr Ile Asp Ala
            180                 185                 190

Ser Tyr Thr Lys Glu Asn Phe Glu Asp Glu Val Pro Phe Ala Gly Phe
        195                 200                 205

Asp Pro Glu Leu Ala Leu Ser Ser Ile Lys Arg Leu Lys Gly Val Val
    210                 215                 220

Ala Glu Glu Lys Pro Ile Val Phe Phe Gly His Asp Ile Glu Gln Glu
225                 230                 235                 240

Lys Gly Cys Arg Val Phe Pro Glu Tyr Ile
                245                 250
```

<210> SEQ ID NO 20
<211> LENGTH: 250
<212> TYPE: PRT
<213> ORGANISM: Bacillus thuringiensis B25

<400> SEQUENCE: 20

```
Met Thr Val Lys Lys Leu Tyr Phe Ile Pro Ala Gly Arg Cys Met Leu
1               5                   10                  15

Asp His Ser Ser Val Asn Gly Thr Leu Ala Pro Gly Asn Leu Leu Asn
            20                  25                  30

Leu Pro Val Trp Cys Tyr Leu Leu Glu Thr Glu Glu Gly Ala Ile Leu
        35                  40                  45

Val Asp Thr Gly Met Pro Glu Ser Ala Val Asn Asn Glu Gly Leu Phe
    50                  55                  60

Asn Gly Thr Phe Val Glu Gly Gln Ile Leu Pro Lys Met Thr Glu Glu
65                  70                  75                  80
```

-continued

```
Asp Arg Ile Val Asn Ile Leu Lys Arg Val Gly Tyr Glu Pro Asp Asp
                85                  90                  95

Leu Leu Tyr Ile Ile Ser Ser His Leu His Phe Asp His Ala Gly Gly
            100                 105                 110

Asn Gly Ala Phe Thr Asn Thr Pro Ile Ile Val Gln Arg Thr Glu Tyr
        115                 120                 125

Glu Ala Ala Leu His Arg Glu Glu Tyr Met Lys Glu Cys Ile Leu Pro
    130                 135                 140

His Leu Asn Tyr Lys Ile Ile Glu Gly Asp Tyr Glu Val Val Pro Gly
145                 150                 155                 160

Val Gln Leu Leu Tyr Thr Pro Gly His Ser Pro Gly His Gln Ser Leu
                165                 170                 175

Phe Ile Glu Thr Glu Gln Ser Gly Ser Val Leu Leu Thr Ile Asp Ala
            180                 185                 190

Ser Tyr Thr Lys Glu Asn Phe Glu Asp Glu Val Pro Phe Ala Gly Phe
        195                 200                 205

Asp Pro Glu Leu Ala Leu Ser Ser Ile Lys Arg Leu Lys Gly Val Val
    210                 215                 220

Ala Lys Glu Lys Pro Ile Val Phe Phe Gly His Asp Ile Glu Gln Glu
225                 230                 235                 240

Lys Gly Cys Arg Val Phe Pro Glu Tyr Ile
                245                 250


<210> SEQ ID NO 21
<211> LENGTH: 256
<212> TYPE: PRT
<213> ORGANISM: Agrobacterium tumefaciens

<400> SEQUENCE: 21

Met Leu Gln Ser Gly Thr Leu Lys Cys Lys Val His Asn Ile Lys Met
1               5                   10                  15

Asn Gln Gly Asn Gly Ala Asp Tyr Glu Ile Pro Val Pro Phe Phe Leu
            20                  25                  30

Ile Thr His Pro Ala Gly His Thr Val Ile Asp Gly Gly Asn Ala Ile
        35                  40                  45

Glu Val Ala Thr Asp Pro Arg Gly His Trp Gly Gly Ile Cys Asp Val
    50                  55                  60

Tyr Trp Pro Val Leu Asp Lys Asp Gln Gly Cys Val Asp Gln Ile Lys
65                  70                  75                  80

Ala Leu Gly Phe Asp Pro Ala Asp Val Lys Tyr Val Val Gln Ser His
                85                  90                  95

Leu His Leu Asp His Thr Gly Ala Ile Gly Arg Phe Pro Asn Ala Thr
            100                 105                 110

His Ile Val Gln Arg Ser Glu Tyr Glu Tyr Ala Phe Thr Pro Asp Trp
        115                 120                 125

Phe Ala Gly Gly Gly Tyr Ile Arg Lys Asp Phe Asp Lys Pro Gly Leu
    130                 135                 140

Lys Trp Gln Phe Leu Asn Gly Ala Gln Asp Asp Tyr Tyr Asp Val Tyr
145                 150                 155                 160

Gly Asp Gly Thr Leu Thr Thr Ile Phe Thr Pro Gly His Ala Pro Gly
                165                 170                 175

His Gln Ser Phe Leu Val Arg Leu Pro Asn Ser Lys Pro Leu Leu Leu
            180                 185                 190

Thr Ile Asp Ala Ala Tyr Thr Leu Asp His Trp Glu Glu Lys Ala Leu
```

```
        195                 200                 205

Pro Gly Phe Leu Ala Ser Thr Val Asp Thr Val Arg Ser Val Gln Lys
    210                 215                 220

Leu Arg Thr Tyr Ala Glu Lys His Asp Ala Thr Val Val Thr Gly His
225                 230                 235                 240

Asp Pro Asp Ala Trp Ala Asn Phe Lys Lys Ala Pro Glu Phe Tyr Ala
                245                 250                 255


<210> SEQ ID NO 22
<211> LENGTH: 248
<212> TYPE: PRT
<213> ORGANISM: Bacillus sp. 240B1

<400> SEQUENCE: 22

Met Thr Val Lys Lys Leu Tyr Phe Val Pro Ala Gly Arg Cys Met Leu
1               5                   10                  15

Asp His Ser Ser Val Asn Ser Thr Leu Thr Pro Gly Glu Leu Leu Asp
            20                  25                  30

Leu Pro Val Trp Cys Tyr Leu Leu Glu Thr Glu Glu Gly Pro Ile Leu
        35                  40                  45

Val Asp Thr Gly Met Pro Glu Ser Ala Val Asn Asn Glu Gly Leu Phe
    50                  55                  60

Asn Gly Thr Phe Val Glu Gly Gln Val Leu Pro Lys Met Thr Glu Glu
65                  70                  75                  80

Asp Arg Ile Val Asn Ile Leu Lys Arg Val Gly Tyr Glu Pro Glu Asp
                85                  90                  95

Leu Leu Tyr Ile Ile Ser Ser His Leu His Phe Asp His Ala Gly Gly
            100                 105                 110

Asn Gly Ala Phe Ile Asn Thr Pro Ile Ile Val Gln Arg Ala Glu Tyr
        115                 120                 125

Glu Ala Ala Gln His Ser Glu Glu Tyr Leu Lys Glu Cys Ile Leu Pro
    130                 135                 140

Asn Leu Asn Tyr Lys Ile Ile Glu Gly Asp Tyr Glu Val Val Pro Gly
145                 150                 155                 160

Val Gln Leu Leu His Thr Pro Gly His Thr Pro Gly His Gln Ser Leu
                165                 170                 175

Leu Ile Glu Thr Glu Lys Ser Gly Pro Val Leu Leu Thr Ile Asp Ala
            180                 185                 190

Ser Tyr Thr Lys Glu Asn Phe Glu Asn Glu Val Pro Phe Ala Gly Phe
        195                 200                 205

Asp Ser Glu Leu Ala Leu Ser Ser Ile Lys Arg Leu Lys Glu Val Val
    210                 215                 220

Met Lys Glu Lys Pro Ile Val Phe Phe Gly His Asp Ile Glu Gln Glu
225                 230                 235                 240

Arg Gly Cys Lys Val Phe Pro Glu
                245
```

BACTERIAL STRAINS, GENES AND ENZYMES FOR CONTROL OF BACTERIAL DISEASES BY QUENCHING QUORUM-SENSING SIGNALS

FIELD OF THE INVENTION

The present invention relates to genes encoding regulators of bacterial metabolism, more particularly to genes encoding enzymes that quench quorum-sensing signals. The present invention further relates to methods of control of bacterial diseases comprising expression of genes encoding autoinducer inhibitors.

BACKGROUND OF THE INVENTION

N-acyl-homoserine lactones, known as autoinducers (AIs), are widely conserved signal molecules present in quorum-sensing systems of many Gram-negative bacteria. It has been found that AIs are involved in the regulation of a range of biological functions, including bioluminescence in *Vibrio* species (Eberhard et al., 1981; Cao and Meighen, 1989), Ti plasmid conjugal transfer in *Agrobacterium tumefaciens* (Zhang et al., 1993), induction of virulence genes in *Erwinia carotovora, Erw. chrysanthemi, Erw. stewartii, Pseudomonas aeruginose, P. solanacerum*, and *Xenorhabdus nematophilus* (Jones et al., 1993; Passador et al., 1993; Pirhonen et al., 1993; Pearson et al., 1994; Beck von Bodman and Farrand, 1995; Flavier et al., 1998; Costa and Loper, 1997; Nasser et al., 1998;), regulation of antibiotic production in *P. aureofaciens* and *Erw. carotovora* (Costa and Loper, 1997; Pierson et al., 1994), regulation of swarming motility in *Serratia liquifaciens* (Eberl et al., 1996), and biofilm formation in *P. fluorescens* and *P. aeruginosa* (Allison et al., 1998; Davies et al., 1998). Many more bacterial species are known to produce AIs, but the relevant biological functions have not yet been established (Bassler et al., 1997; Dumenyo et al., 1998; Cha et al., 1998). Biofilm formation is of particular significance to bacterial pathogenicity, as it makes bacteria more resistant to antibiotics and host defense responses, and causes microbial contamination in medical devices and in drinking water pipelines.

Different bacterial species may produce different AIs. All AI derivatives share identical homoserine lactone moieties, but differ in the length and structure of their acyl groups. Although the target genes regulated by AIs are extremely varied, the basic mechanism of AIs biosynthesis and gene regulation seems to be conserved in different bacteria. The general feature of gene regulation by AIs is cell density dependence, also known as quorum sensing. At low cell densities the AIs are at low concentrations, and at high cell densities the AIs can accumulate to a concentration sufficient for activation of related regulatory genes (Fuqua and Winans, 1996). The biological functions regulated by AIs are of considerable scientific, economic, and medical importance. New approaches for up or down regulation of bacterial quorum sensing systems would be of significant value, not only in science, but also in practical applications.

It has been reported recently that a novel gene encoding autoinducer inactivation (aiiA) has been cloned from the Gram-positive bacterium *Bacillus* sp. strain 240B1 (Dong et al., 2000). Expression of the aiiA in transformed *Erw. carotovora* strain SCG1, a pathogen that causes soft rot disease in many plants, significantly reduces the release of AI, decreases extracellular pectrolytic enzyme activities, and attenuates pathogenicity on potato, eggplant, Chinese cabbage, carrot, celery, cauliflower, and tobacco. The results indicate the promising potential of using the AI-inactivation approach for prevention of diseases in which virulence is regulated by quorum sensing signals.

SUMMARY OF THE INVENTION

Bacterial strains and enzymes capable of efficient inactivation of N-acyl homoserine lactone autoinducers (AIs) are of considerable interest for biotechnology applications. With the present invention it is disclosed that all *Bacillus thuringiensis* strains and their closely related species tested were capable of enzymatic inactivation of AIs. One AI synthesis minus mutant of *Agrobacterium tumefaciens* strain A6, caused by Tn5 insertion mutagenesis, was also found capable of producing AI inactivation enzyme. The genes encoding for AI inactivation enzymes were cloned either by a functional cloning approach or by a PCR approach from the selected bacterial strains. A peptide sequence comparison indicates that all of these enzymes belong to the metallohydrolase family, with amino acid identity ranging from 35.4%-94.0% to the previously reported AiiA enzyme. The *B. thuringiensis* strains effectively quench AI activity when co-cultured with AI producing pathogenic bacteria, and provide effective biocontrol of potato soft rot disease caused by *Erwinia carotovora*. The data suggest that quenching biosignals which regulate virulence is an useful strategy for disease control, and that *B. thuringiensis* strains which are known for insecticidal activity are also promising biocontrol agents for prevention of diseases in which virulence is regulated by AIs.

BRIEF DESCRIPTION OF THE DRAWINGS

FIG. 4 shows (A) the nucleotide sequence (SEQ ID NO 1) and (B) predicted peptide sequence (SEQ ID NO 11) of the aiiB gene cloned from *A. tumefaciens* M103. The putative ribosome binding (SD) region and two PstI restriction enzyme sites are underlined, and the putative transcription termination codon is indicated.

FIG. 5 shows the protein sequence comparison of AiiB (SEQ ID NO 11) and AttM (SEQ ID NO 21), a putative protein encoded by the attM gene in the att region of *A. tumefaciens*, but its biological function has not been demonstrated experimentally (GenBank accession No. U59485). These two proteins exhibit a high degree of similarity (the center sequence represents the consensus sequence, four fragments identical to amino acids 8-43, 45-158, 160-186 and 188-263 of SEQ ID NO 11), but functional AiiB protein has an additional 7 amino acids in the N-terminus.

FIG. 6 shows a protein sequence comparison of AiiB (SEQ ID NO 11) and AiiA (SEQ ID NO 22), a putative metallohydrolase which inactivates AI cloned from *Bacillus* sp. 240B1. The two conserved zinc binding regions are underlined.

FIG. 8 shows (A) the nucleotide sequence (SEQ ID NO 2) and (B) predicted peptide sequence (SEQ ID NO 12) of the aiiC gene cloned from the Bt strain Cot1. The nucleotide sequence of the aiiC ORF is indicated by the uppercase letters and the untranslated regions are indicated by the lower case letters.

FIG. 9 shows the nucleotide sequences and predicted protein sequences of the genes aiiD (SEQ ID NOS 3 & 13), aiiE (SEQ ID NOS 4 & 14), aiiF (SEQ ID NOS 5 & 15), aiiG (SEQ ID NOS 6 & 16), aiiH (SEQ ID NOS 7 & 17), aiiI (SEQ ID NOS 8 & 18), aiiJ (SEQ ID NOS 9 & 19) and aiiK (SEQ ID NOS 10 & 20) from Bt strains B1, B2, B17, B18, B20, B21, B22 and B25, respectively.

DETAILED DESCRIPTION OF THE INVENTION

Figure 1:
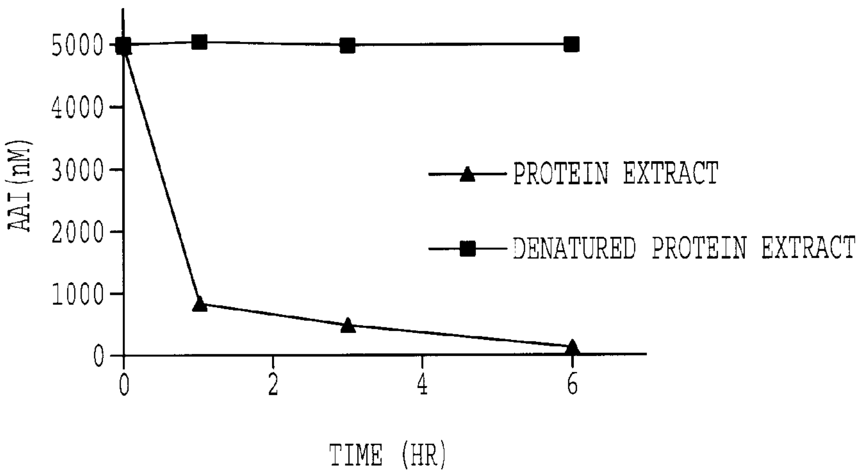
FIG. 1 shows the time course of AI (OOHL) inactivation by the protein extract of *A. tumefaciens* strains M103. The total protein of M103 was extracted by sonication disruption of bacterial cells in 1/15 M phosphate buffer (pH 8.0). Equal volumes of M103 protein extract (1.46 mg/ml) and 5000 nM OOHL were mixed and incubated in a 1.5 ml Eppendorf centrifuge tube at 28° C. Same protein extract was denatured by boiling for 5 min and used as a control. The samples were taken after 1, 3, 6 hr after reaction and the reaction was stopped by boiling for 3 min. The samples were analyzed for AI activity.

Ten genes encoding AI inactivation enzymes have been cloned from 9 Gram positive bacterial isolates and one Gram negative bacterium (*A. tumefaciens*). The genes showed different levels of homologies to the aiiA gene, which encodes a putative metallohydrolase with strong AI inactivation activity (Dong et al., 2000). Similar to AiiA, the zinc binding motif regions are highly conserved in the enzyme proteins encoded by these newly cloned AI inactivation genes. It is very likely that these the enzymes are also members of the metallohydrolase family, and use the same molecular mechanism as the AiiA for inactivation of N-acyl homoserine lactone autoinducers. The present invention further enriches the gene pool of AI inactivation enzymes.

In *A. tumefaciens*, N-acyl homoserine lactone autoinducers, mainly OOHL, are involved in regulation of Ti plasmid conjugal transfer (Zhang et al., 1993). The production of OOHL in *A. tumefaciens* is induced by the conjugal opines secreted by crown gall tumours (Zhang and Kerr, 1991). The OOHL in turn induces the expression of tra genes. The proteins are responsible for completing the process of Ti plasmid conjugal transfer. Only a few hours are required from opine induction to completion of Ti plasmid conjugal transfer, so the Ti plasmid conjugal transfer can therefore be regarded as only a transient event. One embodiment of the present invention, the aiiB gene for N-acyl homoserine lactone degradation, identified in *A. tumefaciens*, highlights the possibility that the bacterium has a sophisticated mechanism for control of AI signal turn over. It is plausible that AI is degraded in *Agrobacterium* after completion of the Ti plasmid conjugal transfer.

It has been noted that a majority of bacterial isolates capable of AI inactivation are Gram positive, belonging to *B. thuringenesis* and closely related species. So far, most of the characterised quorum-sensing signals in Gram-negative bacteria are N-acyl homoserine lactones (Fuqua et al., 1996), while Gram-positive bacteria produce oligopeptides as quorum-sensing signals (Dunny and Leonard, 1997).

*Bacillus thuringiensis* (Bt) has been used extensively as a microbial insecticide during the last 30 years. The microorganism is a gram-positive, spore-forming soil bacterium, and produces a crystalline parasporal body consisting of one or more crystal (Cry) proteins during sporulation, which shows biocidal activity against insect families such as lepidopteran, dipteran, and colepteran insects at larval stages (Lambert and Peferoen, 1992). Some Bt strains have also been reported to be active against other insect families, as well as mites, nematodes, flatworms, and protozoa (Feitelson et al., 1992). Different Bt strains produce more than 28 different but related groups of insecticidal crystal proteins (http://www.biols.susx.ac.uk/Home/Neil_Crickmore/Bt/). Different groups of crystal proteins are usually active against a specific spectrum of insects, but do not affect other beneficial insects in agriculture. Currently, Bt-based formulations are the most widely used and most effective microbial insecticides in agriculture.

As a valuable biocontrol agent, Bt has several advantages including its specificity for target insects, its low development cost, and its environmental compatibility (Lambert and Peferoen, 1992). Bt is commonly found in natural soil, and normally multiplies by cell division, but forms spores when nutrients are depleted or when the environment becomes adverse. These spores are highly resistant to stress conditions such as heat and drought, enabling the bacterium to survive periods of stress. This sporulating Gram-positive micro-organism can be formulated readily into stable products, such as a dry powder, for insect or disease biocontrol. Bt also has been subjected to many safety tests, with no harmful effects for animals or human beings.

Bt has not been exploited for disease control because it usually does not produce effective antibiotics against bacteria and fungi. In the present invention, it has been found that all tested Bt strains are capable of inactivating AI, and that Bt strains provide effective biocontrol against *Erw. carotovora* infection, whereas *B. fusiformis* and *E. coli* strains which do not have AI inactivation genes were unable to provide biocontrol against *Erw. carotovora*. Bt strains did not produce any antibiotics and were not inhibitory to the growth of pathogen. The data strongly suggest the important role of AI inactivation genes in disease biocontrol. Because the AI diffuses easily into bacterial cells, Bt, capable of eliminating AI constantly from its surroundings, is a promising biocontrol agent, not only for control of plant soft rot disease caused by *Erw. carotovora*, but also for control of other diseases in which the virulence genes are regulated by AIs.

Accordingly, an object of the present invention is to provide a method for increasing resistance in a plant or animal to a disease in which virulence is regulated by AIs [such as the diseases caused by *Pseudomonas aeruginosa, Erwinia stewartii, Erwinia chrysanthemi, Pseudomonas solanacerum*, and *Xanthomonas campestris* ( Passador, et al., 1993; Pirhonen, et al., 1993; Pearson, et al., 1994; Beck von Bodman and Farrand, 1995; Barber, et al., 1997; Clough, et al., 1997; Costa and Loper, 1997; Nasser, et al., 1998), and especially plant soft rot disease caused by *Erw. carotovora]* comprising administering to the plant or animal an effective amount of a bacterium that is capable of producing an autoinducer inhibitor. In a preferred embodiment of this aspect of the invention, the bacterium administered is a *Bacillus* sp., more preferably a variety of *Bacillus thuringiensis*, most preferably a variety of *B. thuringiensis* selected from the group consisting of B1, B2, B17, B18, B20, B21, B22 and B25. In another preferred embodiment of this aspect of the invention, the animal to be treated is a human.

It is another object of the present invention to provide isolated nucleic acid molecules encoding autoinducer inactivation proteins. These nucleic acid molecules encode autoinducer inactivation proteins that share the conserved amino acid motif $^{104}HXHXDH^{109}$~59aa~$H^{169}$~21aa~$D^{191}$, or the similar motif $^{103}HXHXDH^{108}$~71aa~$H^{180}$~21aa~$D^{202}$. Preferred embodiments of these nucleic acid molecules encode the proteins of SEQ ID NOS 11-20, and most preferred embodiments of these nucleic acid molecules have the sequences of SEQ ID NOS 1-10.

Another object of the present invention is to provide an expression vector that comprises at least one nucleic acid sequence encoding an autoinducer inactivation protein, wherein the encoded protein comprises the conserved amino acid motif $^{104}HXHXDH^{109}$~59aa~$H^{169}$~21aa~$D^{191}$, or the similar motif $^{103}HXHXDH^{108}$~71aa~$H^{180}$~21aa~$D^{202}$, wherein the expression vector propagates in a procaryotic or eucaryotic cell. Preferred embodiments of these expression vectors comprise at least one nucleic acid sequence encoding a protein having a sequence selected from the group consisting of SEQ ID NOS 11-20, and most preferred embodiments have the nucleic acid sequences of SEQ ID NOS 1-10.

Yet another object of the present invention is to provide a cell of a procaryote or eucaryote transformed or transfected with an expression vector of the present invention.

Yet another object of the present invention is to provide an isolated protein which has autoinducer inactivation activity, where the protein comprises the conserved amino acid sequence $^{104}HXHXDH^{109}$~59aa~$H^{169}$~21aa~$D^{191}$, or the similar motif $^{103}HXHXDH^{108}$~71aa~$H^{180}$~21aa~$D^{202}$. Preferred embodiments of the invention comprise proteins having the amino acid sequences of SEQ ID NOS 11-20.

Yet another object of the present invention is to provide a method for increasing disease resistance in a plant or animal, which method comprises introducing into a cell of such plant or animal at least one nucleic acid molecule that encodes an autoinducer inactivation protein in a manner that allows said cell to express said nucleic acid sequence, wherein said autoinducer inactivation protein comprises the conserved amino acid sequence $^{104}HXHXDH^{109}$~59aa~$H^{169}$~21aa~$D^{191}$, or the similar motif $^{103}HXHXDH^{108}$~71aa~$H^{180}$~21aa~$D^{202}$. Preferred embodiments of this aspect of the invention comprise introducing at least one nucleic acid molecule encoding a protein having a sequence selected from the group consisting of SEQ ID NOS 11-20, and most preferred embodiments comprising introducing at least one nucleic acid sequence selected from the group consisting of SEQ ID NOS 1-10.

Yet another object of the present invention relates to a method of preventing or reducing bacterial damage to a plant or animal, which method comprises administering to a plant or animal in need of such prevention or reduction an effective amount of at least one autoinducer inactivation protein, wherein said protein comprises the conserved amino acid sequence $^{104}HXHXDH^{109}$~59aa~$H^{169}$~21aa~$D^{191}$, or the similar motif $^{103}HXHXDH^{108}$~71aa~$H^{180}$~21aa~$D^{202}$. Preferred embodiments of this aspect of the invention comprise providing at least protein having the amino acid sequences of SEQ ID NOS 11-20.

Yet another object of the present invention relates to a method of preventing or reducing the formation of bacterial biofilms, which method comprises exposing biofilm-forming bacteria to at least one autoinducer inhibitor protein, wherein said protein comprises the conserved amino acid sequence $^{104}$HXHXDH$^{109}$~59aa~H$^{169}$~21aa~D$^{191}$, or the similar motif $^{103}$HXHXDH$^{108}$~71aa~H$^{180}$~21aa~D$^{202}$. Preferred embodiments of this aspect of the invention comprise exposing the biofilm-forming bacteria to at least protein having the amino acid sequences of SEQ ID NOS 11-20.

It is possible to further enhance the efficiency of Aii-producing bacterial strains by using a genetic approach to modify such strains, for example by introducing genes encoding for additional, or more active, autoinducer inhibitors. It also is possible to optimise the enzyme activity of aii genes by an in vitro DNA evolution approach. Increasing the expression of Aii enzymes by coupling the aii gene to a strong promoter or increasing the copy number of the aii gene in Bt cells would be another useful way to improve the capacity of Bt strains to quenching AI signals. It is likely that genetically modified Bt strains which secrete AI inactivation enzyme or contain the enzyme in the outer membrane of the cell could have better efficiencies in quenching AI signals than their wild type parent stain. This is achievable by fusing an aii gene to a sequence encoding a secretion or a membrane attachment signal peptide.

The sequence may be introduced into plant or animal cells by well-known methods. Methods for the transformation or transfection of eukaryotic cells with exogenous nucleic acid sequences include transfection, projectile bombardment, electroporation or infection by *Agrobacterium tumefaciens*. These methods are likewise familiar to the person skilled in the area of molecular biology and biotechnology and need not be explained here in detail.

As pathogenic bacteria cells are confined to the intercellular area of plant tissues, it is desirable to target the Aii protein into the intercellular spaces. Such may be accomplished by fusing a secretion signal peptide to the Aii protein (Sato, et al., 1995; Firek, et al., 1993; Conrad and Fiedler, 1998; Borisjuk, et al., 1999). Alternatively, a plant membrane attachment motif can be incorporated into the peptide sequence of Aii for anchoring the Aii enzyme in the outer surface of plant cell membrane.

The present invention also contemplates usage of a bacterial autoinducer inactivation protein directly to treat or present bacterial damage. For example, the protein may be applied directly to plants in need of such treatment or prevention. In a preferred embodiment, the protein is applied in the form of a composition which comprises an effective amount of the protein and a suitable carrier. The composition may have a wide variety of forms, including solutions, powders, emulsions, dispersions, pastes, aerosols, etc.

The bacterial autoinducer inactivation protein may also be used to treat bacterial infections in animals, including humans. In that application, an effective amount of the active ingredient is administered to an animal in need of such treatment.

For therapeutic treatment, the active ingredient may be formulated into a pharmaceutical composition, which may include, in addition to an effective amount of the active ingredient, pharmaceutically acceptable carriers, diluents, buffers, preservatives, surface active agents, and the like. Compositions may also include one or more other active ingredients if necessary or desirable.

The pharmaceutical compositions of the present invention may be administered in a number of ways as will be apparent to one of ordinary skill in the art. Administration may be done topically, orally, by inhalation, or parenterally, for example. Topical formulations may include ointments, lotions, creams, gels, drops, suppositories, sprays, liquids and powders. Oral formulations include powders, granules, suspensions or solution in water or non-aqueous media, capsules or tablets, for example. Thickeners, flavorings, diluents, emulsifiers, dispersing aids or binders may be used as needed. Parenteral formulations may include sterile aqueous solutions which may also contain buffers, diluents and other suitable additives. The does regimen will depend on a number of factors which may readily be determined, such as severity and responsiveness of the condition to be treated.

Traditionally, microbial biocontrol has depended on production of antibiotics or antimicrobial compounds (Cronin et al., 1997; Liao an Sapers, 1999; Emmert and Handelsman, 1999). The present invention offers an alternative strategy for biocontrol, based on quenching biosignals that are essential for virulence.

EXAMPLE 1

Bacterial Strains Capable of Inactivating Autoinducers

To identify the genes responsible for inactivation of autoinducer signals, more than 400 field and plant bacterial isolates and about 100 strains of the laboratory bacterial culture collection were screened. The bacterial strains used to test the ability of inactivating autoinducer signals were isolated from soil and plant suspensions as described previously (Dong et al., 2000), or obtained from *Bacillus* Genetic Stock Centre (BGSC) and the American Type Culture collection (ATCC). *Erwinia carotovora* SCG1 was isolated from Chinese cabbage leaves showing soft rot symptoms. It was confirmed by 16S DNA sequence and its characteristic production of autoinducer and induction of soft rot disease in potato and Chinese cabbage. These strains were grown at 28° C. in Luria-Bertani (LB) medium with shaking when necessary. *Agrobacterium tumefaciens* strains were grown at 28° C. in YEB, in BM minimal medium (basic minimal nutrient added with mannitol as sole carbon source), or on nutrient agar plates (Difco Laboratories). Mannitol at a final concentration of 0.2% was used as the sole carbon source in the minimal medium. *Escherichia coli* strains were grown at 37° C. in LB or on LB agar plates. Antibiotics were added at the following concentrations, when required: rifampin at 50 μg/ml, streptomycin at 100 μg/ml, ampicilin at 100 μg/ml, kanamycin at 50 μg/ml, and tetracycline at 10 μg/ml. X-gal (5-bromo-4-chloro-3-indolyl-B-D-galactopyranoside) (Promega) was included in media at 50 μg/ml for detection of β-galactosidase enzyme activity.

More than 30 strains showed different levels of AI inactivation activity. To characterise the unknown isolates, the 16S rRNA sequences of these isolates were analysed by PCR amplification and subsequent sequencing. The sequence search showed the 16S rRNA sequences of those strains capable of inactivation AI are highly homologous to that of *Bacillus thuringiensis* (Bt).

To test whether other *Bacillus* strains also have the AI-inactivation ability, known strains of *B. thuringenesis, B. cereus, B. mycoides*, and *B. sphaericus* were selected for bioassay. For determination of the AI inactivation ability of bacterial strains and isolates, the autoinducer, N-β-oxo-hexanoyl-L-homoserine lactone (OHHL), or N-β-oxo-octanoyl- L-homoserine lactone (OOHL) was added to the over-night bacterial cultures which were diluted to $OD_{600}$=1.1, or to the protein extracts, at a final concentration of 20 μM, and incubated at 28° C. for 30 min. The AI remaining in the supernatant was then determined as previously described (Zhang, 1993; Dong et al., 2000).

Table 1 shows the AI inactivation activities of the selected strains and some newly identified isolates. All the tested bacterial strains, except *B. sphaericus* and *B. fusiformis*, eliminated AI (at a concentration of 20 μM OHHL) with different levels of enzyme activities. These strains include 13 known *Bacillus* species (strains starting with a "B" in Table 1), 1 known *Agrobacterium* and 9 *Bacillus* species identified by 16S rDNA sequence analysis. Among them, 12 bacterial strains showed a high level of AI-inactivation activity (>30 μM/h/$OD_{600}$); 8 showed a medium level of activity (25-30 μM/h/$OD_{600}$); and the *A. tumefaciens* strain M103 showed a low level of activity (4.5 μM/h/$OD_{600}$). Except for *A. tumefaciens*, all these AI-inactivation strains are Gram-positive and belong to *B. thuringenesis* or its close related species.

TABLE 1

Bacterial strains and their AI-inactivation activity

| | Strains | Source | Enzyme activity (μM/h/$OD_{600}$) |
|---|---|---|---|
| 28-32 | *Bacillus thuringiensis* | This work | 32.4 ± 1.1 |
| 258-3 | *Bacillus thuringiensis* | This work | 32.5 ± 1.2 |
| 69 | *Bacillus thuringiensis* | This work | 30.9 ± 2.3 |
| 60-1 | *Bacillus thuringiensis* | This work | 28.2 ± 5.1 |
| 250 | *Bacillus thuringiensis* | This work | 23.4 ± 3.9 |
| 262 | *Bacillus thuringiensis* | This work | 23.1 ± 1.5 |
| B18 | *Bacillus thuringiensis* | This work | 27.4 ± 3.0 |
| B20 | *Bacillus thuringiensis* | This work | 32.7 ± 2.4 |
| B21 | *Bacillus thuringiensis* | This work | 33.1 ± 0.8 |
| B22 | *B. thuringiensis* ssp. *kurstaki** | This work | 32.8 ± 1.3 |
| B23 | *B. thuringiensis* ssp. *Israelensis** | BGSC (4Q7) | 26.7 ± 3.5 |
| B1 | *B. thuringiensis* ssp. *thuringiensis* | BGSC (4A3) | 32.5 ± 0.3 |
| B2 | *B. thuringiensis* ssp. *kurstaki* | BGSC (4D1) | 33.0 ± 0.6 |
| B12 | *B. thuringiensis* ssp. *Aizawai* | BGSC (4J4) | 33.5 ± 0.9 |
| B17 | *B. thuringiensis* ssp. *Wuhanensis* | Mycogen (PSS2A1) | 28.8 ± 4.1 |
| B25 | *Bacillus cereus* | This work | 33.7 ± 0.8 |
| B14579 | *Bacillus cereus* | ATCC (14579) | 31.7 ± 0.6 |
| B6462 | *Bacillus mycoides* | ATCC (6462) | 29.8 ± 2.2 |
| 240B | *Bacillus* sp. | This work | 33.0 ± 1.0 |
| Cot | *Bacillus thuringiensis* | This work | 25.1 ± 2.4 |
| M103 | *Agrobacterium tumefaciens* | This work | 4.5 |
| 269 | *Bacillus fusiformis* | This work | 0 |
| B29 | *Bacillus sphaericus* | BGSC (12A4) | 0 |

*Plasmid minus

**Equal volume bacterial suspension (diluted to $OD_{600}$ = 1.1 from overnight cultures) and OHHL (40 μM) were incubated at 28° C. for 30 min and then OHHL remaining in the supernatant was determined as previously described (Zhang, 1993). The enzyme activity is shown as digested μM of OOHL per hour per $OD_{600}$ of bacterial culture. Values represent mean ± standard deviation of 4 replicates. Strains starting with a "B" prefix are the known *Bacillus* species. Other *Bacillus* strains were identified by 16S rDNA sequence analysis.

The evidence suggests that the AI-inactivation gene is located in chromosomal DNA but not in a plasmid, because Bt ssp. *kurstaki* strain B2 and its plasmid minus derivative strain B22, both showed a similar level of enzyme activity. The second plasmid minus strain B23, belonging to *B. thuringenesis* ssp. *Israelensids*, was also capable of enzymatic inactivation of AI.

To investigate the genetic diversity of genes for AI-inactivation, the representative bacterial strains showing high, medium or low levels of AI-inactivation activity were chosen for further cloning experiments.

EXAMPLE 2

Functional Cloning of the aiiB Gene from *Agrobacterium tumefaciens* Strain M103

The suicide plasmid pSUP10 (Simon et al, 1983) in *E. coli* SM10 was used to introduce transposon Tn5 insertions into the genome of *A. tumefaciens* octopine strain A6 by the protocol described by Garfinkel and Nester (1980), except that the bacterial suspensions were spread onto BM minimal plates containing kanamycin (100 μg/ml). Total DNA of *A. tumefaciens* mutant strain M103 was partially digested with EcoRI, the 20-30 kb fragments were recovered from lower melting point agarose gel and purified. The purified fragments were ligated to the dephosphorized EcoRI site of the cosmid vector pLAFR3 (Staskawicz et al., 1987). The ligation mixture was packaged with GigapackTMIII XL Packaging Extract (Stratagene) and then transfected into *E. coli* DH5α. About 2000 individual colonies grown on the selective medium containing tetracycline were maintained as the genomic library of *A. tumefaciens* mutant strain M103. The cosmid clones containing Tn5 were selected on the medium containing kanamycin and were further assayed for AI inactivation activity by using the bioassay method described above. Subcloning into the sequencing vector pGEM-7Zf(+) was carried out by routine techniques (Sambrook et al., 1989). Sequencing was performed on both strands by using the ABI Prism dRhodamine Terminator Cycle Sequencing Ready Reaction Kit (Perkin-Elmer Applied Biosystems).

*Agrobacterium tumefaciens* strains A6 produces N-acyl homoserine lactone autoinducers (AI) which are involved in regulation of Ti plasmid conjugal transfer (Zhang and Kerr, 1991). But its derivative M103 caused by Tn5 insertional mutagenesis is capable of inactivation of AI. (Table 1 and FIG. 1). It is likely that the gene encoding for AI degradation in strain A6 is regulated by a negative regulator, and the Tn5 insertion resulted in constitutive expression of the gene for AI inactivation.

Figure 2:
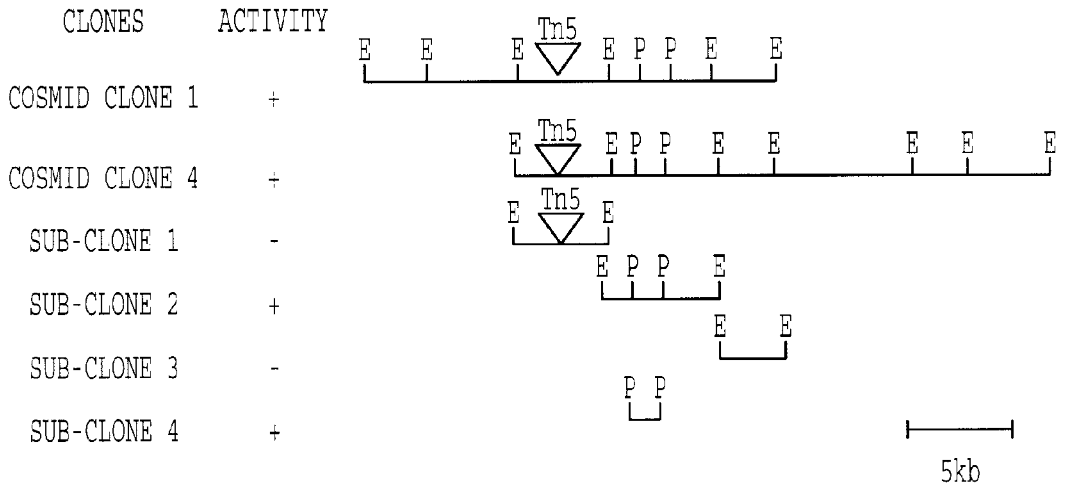
FIG. 2 shows the cloning of the AI inactivation region from the cosmid clones of mutant M103. Two cosmid clones were contained in cosmid vector pLAFR3 while the four subclones in plasmid vector pBluescript II SK(+). Symbols: +, positive in AI inactivation; –, negative in AI inactivation; E: EcoRI; P: PstI.
Figure 3A:
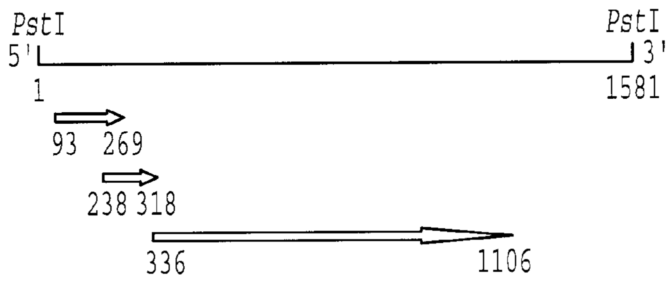
FIG. 3 shows (A) The potential ORFs in the 1.5 kb AI inactivation region predicated with a sequence analysis program; and (B) Deletion analysis to define the ORF encoding AI inactivation enzyme (AiiB). PCR amplified fragments were cloned into vector pBluescript II SK(+) (pBM clones) or in vector pKK223-3 (pKM clones). The numbers under each clone indicate the start and stop positions of the PCR fragments corresponding to the nucleotide sequences of the 1.5 kb region. All constructs were confirmed by sequencing analysis. The start codon (GTG) and stop codon (TAA) of the aiiB ORF are shown under the clone pKM103-315. Solid arrows indicate the location and direction of lac and tac promoter in these clones, the ORFs were indicated with open arrows. Symbols: +, positive AI inactivation activity; –, negative AI inactivation activity.
Figure 3B:
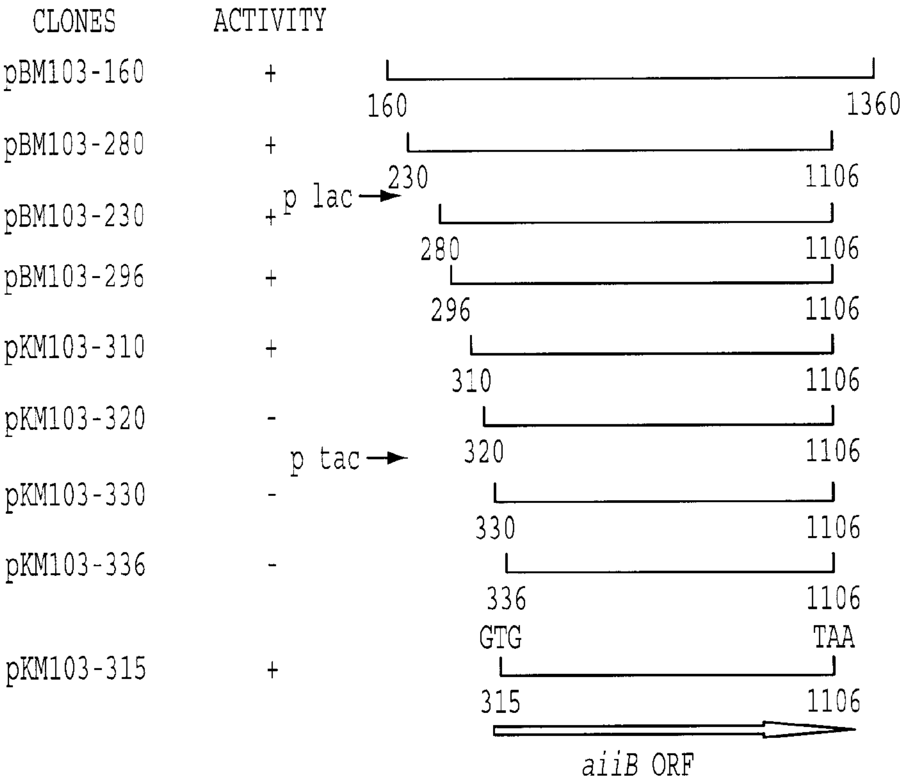

Based on the assumption that the AI inactivation gene may be located downstream of the Tn5 insertion site, the cosmid clones containing Tn5 transposon were selected by the kanamycin resistance phenotype. Two cosmid clones resistant to kanamycin and showing AI inactivation activity were obtained from the cosmid library of M103. Restriction analysis and bioassay showed that a 5.2 kb EcoRI fragment conferred the AI inactivation activity. Further subcloning narrowed down the region to a 1.5 kb PstI fragment (FIG. 2). Sequence analysis showed that several putative open reading frames (ORFs) starting with ATG or UTG were in the fragment. One of the ORFs showed 96.8% identity in nucleotide sequence and 98% in amino acid sequence to the attM gene (U59485) of *A. tumefaciens* identified previously. However, AI inactivation activity was not detected when expressing the attM in *E. coli* via an expression vector pKK223-3. Deletion analysis of the 1.5 kb fragment showed that a 792 bp ORF, its start codon a GTG rather than the normal ATG, encoding for AI inactivation (FIG. 3). The gene was named as aiiB (FIG. 4). In comparison with the AttM whose biological function has not been identified experimentally, the AiiB has 7 extra amino acids at the N terminus (FIG. 5). AiiB showed 35.4% identity at the amino acid level compared to the previously reported AiiA (FIG. 6).

EXAMPLE 3

Functional Cloning of the aiiC Gene from *B. thuringinesis* Strain Cot1

Figure 7A:
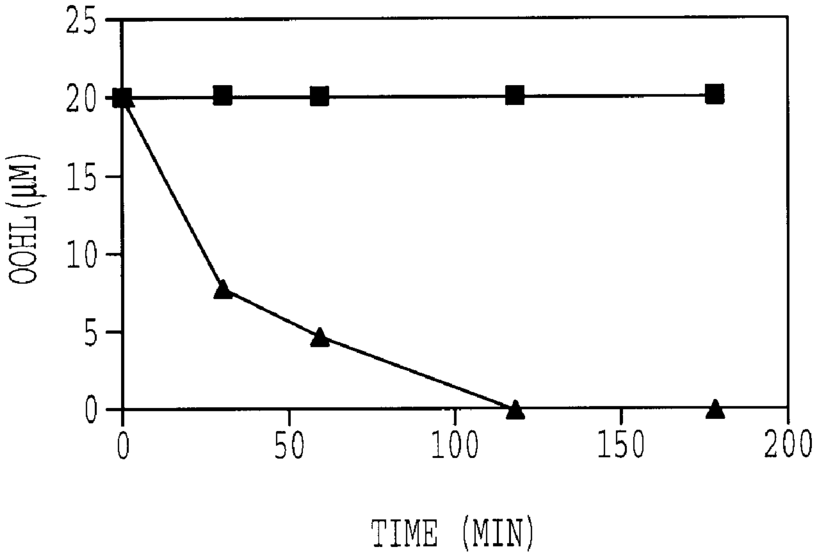
FIG. 7 shows the functional cloning of the aiiC gene. (A) Enzymatic inactivation of AI by the suspension culture of Bt strain Cot1. Equal volume of cell suspension culture ($OD_{600}$=1.1) and 40 μM OOHL were mixed and incubated at 28° C. (▲). The boiled cultures and OOHL at same concentrations were used as control (■). The samples were taken at times as indicated for AI activity assay. (B) Direct subcloning of AI-inactivation regions from the cosmid clones pLAFR3-aiiC of *B. thuringiensis* Cot1. The cosmid clone was digested by EcoRI and subcloned into the pGEM-7Z vector. The AI inactivation positive clone pGEM7-aiiC was identified by enzyme activity assay. The pGEM7-aiiC was further subcloned in the pBluescript II SK(+) vector after BamHI digestion. The AI inactivation region of about 1.4 kb in size contained in clone pBS-aiiC was completely sequenced. Restriction enzymes: E: EcoRI; B: BamHI.

The suspension culture of strain Cot1 eliminated AI (20 μM) completely after 2 hr incubation, but bacterial cells killed by boiling for 5 min failed to inactivate AI (FIG. 7A), indicating an enzymatic inactivation mechanisms. To identify the gene encoding for AI inactivation from Cot1, a cosmid library was constructed by EcoRI partial digestion of the genomic DNA of the bacterial isolate Cot1. Genomic DNA was extracted from bacterial isolate Cot1 and digested partially with EcoRI. The DNA fragments were ligated to the dephosphorylized EcoRI site of cosmid vector pLAFR3. Ligated DNA was packaged and transfected into *E. coli* DH5α. Cosmid clones with AI inactivation activity were identified by using the bioassay method described above. Subcloning into the sequencing vector pGEM-7Zf(+) or pBlueScript SK were carried out by routine techniques.

Figure 7B:
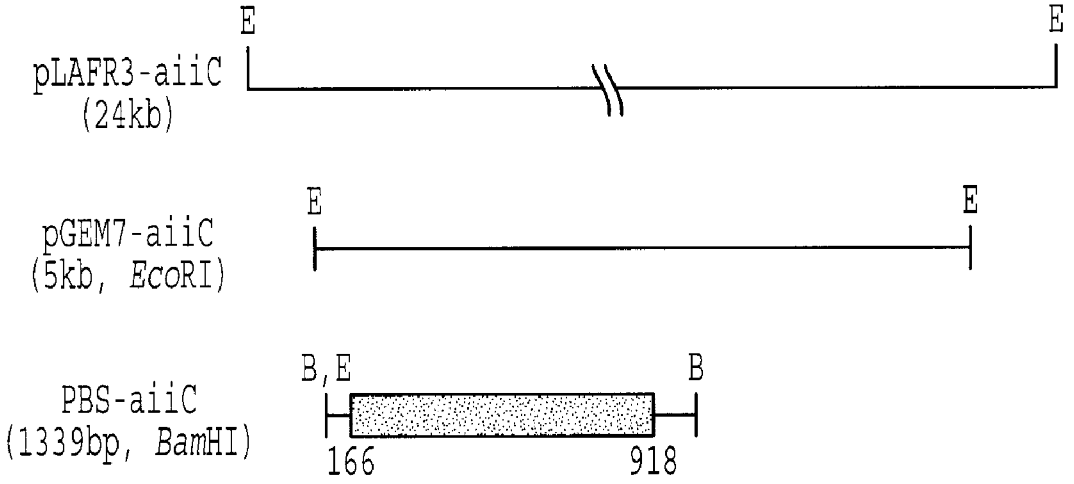

One clone showing AI inactivating function was identified from the one thousand cosmid clones screened. Restriction analysis showed that this clone contains an insert of 24 kb. All five fragments generated by EcoRI complete digestion were subcloned into pGEM7 vector. The bioassay of these subclones showed that one clone, pGEM7-aiiC with an insert of 5 kb, conferred the AI inactivation activity. Further subcloning identified a 1.4 kb BamHI fragment contained in the clone pBS-AiiC which was responsible of the AI inactivation function (FIG. 7B). The complete sequence of the clone pBS-AiiC showed that there is an ORF of 750 bp nucleotides (from 166 to 918) which encodes a protein of 250 amino acids (FIG. 8). Cloning of this ORF in the *E. coli* expression vector confirmed that it encoded a functional AI inactivation enzyme, designated as AiiC. At the peptide sequence level, the AiiC gene showed 91% and 33% identity, to the AiiA and the AiiB respectively. The aiiC gene has no significant similarity to other known sequences in the databases by FASTA and BLAST analysis at either nucleotide or peptide levels.

EXAMPLE 4

The Autoinducer Inactivation Genes in Bt Belong to the Same Gene Family

Among the tested bacterial isolates with AI inactivation activity, all except the *A. tumefaciens* strains M103, are Gram positive, and belong to *B. thuringiensis* (Bt) or closely related bacterial species. The aiiA and aiiC genes from the two *Bacillus* strains showed a high level of similarity. It is very likely that the aiiA and aiiC genes are highly conserved among *B. thuringiensis* strains. DNA hybridisation (Southern blot) analysis was performed using an aiiC fragment as a probe. The genomic DNA was isolated from 18 selected bacterial strains, B1(Bt ssp. *thuringiensis*), B2, B3 and B4 (Bt ssp. *kurstaki*), B22 (Bt ssp. *kurstaki* plasmid minus), B12 (Bt ssp. *Aizawai*), B16 and B17 (Bt ssp. *Wuhanensis*), B23 (Bt ssp. *Israelensis*), and other Bt strains B18, B20, B21, 240B1, 471W, and Cot1 as well as B25 and B26 (*B. cereus*), and B29 (*B. sphaericus*). Genomic DNA (20 μg) digested with EcoRI was separated by electrophoresis in 0.8% agarose gel and then the DNA was transferred onto Hybond−N+ membrane (Amersham Pharmacia, Biotech.) according to manufacture's instructions. The 1.4 kb BamHI fragment containing the aiiC codon region was labelled with DIG for use as a probe for hybridisation. After hybridisation at 65° C., the membrane was washed twice in 2 x SSC, 0.1% SDS at room temperature for 5 min, followed by washing twice in 0.1 x SSC, 0.1 x SDS at 65° C. for 15 minutes. After washing, the membrane was detected with anti-DIG-AP conjugate, the NBT/BCIP solution was used as colour substrate according to manufacture's protocol (Boehringer Mannheim).

The result showed that one hybridising band was clearly detected from all tested strains, except for B29 (*B. sphaericus*). These results indicated that there is a single gene, with sequence similar to aiiC, present in all tested *B. thuringiensis* strains and its closely related species *B. cereus*. This is in agreement with the bioassay data (Table 1).

EXAMPLE 5

Cloning of Other AI Inactivation Genes from more Bacterial Isolates

Since the genes for AI inactivation are highly conserved, a PCR approach was used for the clinging of other AI inactivation genes from the selected *B. thuringiensis* isolates. Genomic DNA isolated from the bacterial isolates B1, B2, B17, B18, B20, B21, B22 and B25 was used as template. Primers were designed based on the conserved sequences of the 5' and 3' ends of the aiiA and aiiC gene. Standard PCR conditions were used to amplify AI-inactivation genes from the selected bacterial isolates. The primer sequences were: C5f: 5'-ATG GGA TCC ATG ACA GTA AAG AAG CTT TAT-3'; C3r: 5'-GTC GAA TTC CTC AAC AAG ATA CTC CTA ATG-3'. The PCR reactions were performed for 35 cycles of 30 sec at 94° C., 30 sec at 55° C. and 1 min at 72° C. using a Perkin Elmer GenAmp PCR System 2400. Two separate PCR reactions were performed to make sure there was no error in the amplified sequences. The PCR products were purified by using QIAquick PCR Purification Kit (QIAGEN) and the purified PCR fragment was ligated to pGEM-T vector (Promega). Clones having inactivating autoinducer activity were chosen for further study. Two such clones from each strain were sequenced. Nucleic acid sequence data and deduced amino acid sequences were analysed with the DNASTARTM sequence analysis software package (DNASTAR Inc.) and GCG sequence analysis software (Genetics Computer Group, Wisconsin). Database searches were performed using the BLASTA search algorithm.

FIG. 9 shows the nucleotide and deduced peptide sequences of 8 AI inactivation genes (named aiiD to aiiK) cloned from Bt strains B1, B2, B17, B18, B20, B21, B22 and B25 respectively. These sequences all contain an ORF of 750 bp, which encodes a protein of 250 amino acids.

EXAMPLE 6

The Autoinducer Inactivation Genes are Highly Conserved Among Members of Bt and Closely Related *Bacillus* ssp.

Figure 10:
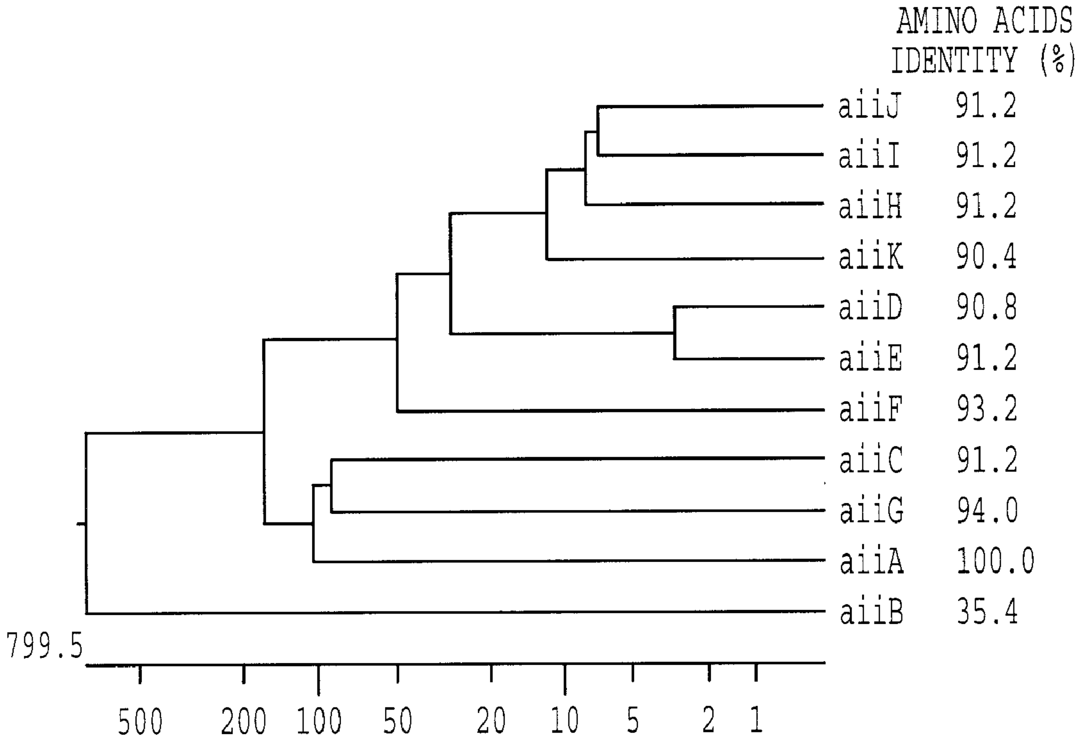
FIG. 10 shows a phylogenetic tree analysis and amino acid identity of 11 cloned AI inactivation genes. The phylogenetic tree was produced by DNASTAR sequence analysis software (DNASTAR Inc.). The distance is shown below the tree. The amino acid identity of each sample to AiiA is shown at the right hand of the graph.

Except for the aiiB gene, all other genes were cloned from the Gram positive bacterial isolates. Sequence analysis indicated that the aii genes cloned from the Gram positive bacterial isolates are highly conserved, with high amino acid identities ranging from 90.4% to 94.0%, in comparison to that of AiiA (FIG. 10). The aiiB gene cloned from the Gram negative *A. tumefaciens* showed less similarity to other aii genes and clustered as a signal group in the phytogenetic tree (FIG. 10).

These results indicate that the autoinducer inactivation genes are highly conserved among members of Bt and closely related *Bacillus*.

In these Aii protein sequences, all except AiiB contain several invariant histidines with glutamate residues showing a pattern of $^{104}HXHXDH^{109}$~59aa~$H^{169}$~21aa~$D^{191}$; the AiiB of *A. tumefaciens* contains the similar, but distinct motif $^{103}HXHXDH^{108}$~71aa~$H^{180}$~21aa~$D^{202}$. This pattern agrees with the metallohydrolase criterion (Vallee and Galdes, 1984). The motif HXHXDH in the *Arabidopsis* glyoxalase II was suggested to be involved in binding to zinc ion (Crowder et al., 1997). Site-directed mutagenesis has shown that all these residues except the first histidine ($^{104}H$ in AiiA) in this motif are necessary for AiiA activity. These invariant histidines and glutamate residues are also present in AiiB to AiiK, indicating they belong to the same group of autoinducer metallohydrolases.

EXAMPLE 7

Effect of Bt Strains on AI Production by *Erwinia carotovora*

Figure 11:
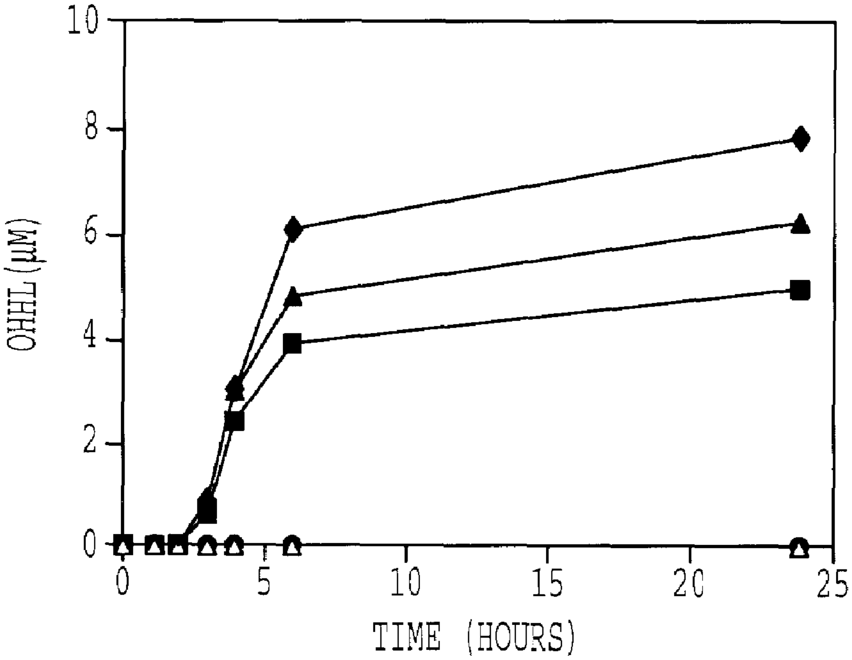
FIG. 11 shows the effect of Bt strains on AI production by *Erwinia carotovora. Erw. carotovora* SCG1 was inoculated alone in 15 ml LB medium (♦) or co-inoculated respectively in 1:1 ratio with Bt strains Cot1 (Δ) and B1 (●), *E. coli* DH5α (▲) and *B. fusiformis* (■) in the same medium. The inoculum concentration ($T_0$) was $1\times10^7$ CFU/ml (colony forming unit per milliliter) for SCG1 and $1\times10^6$ CFU/ml for others. After incubation of 1, 2, 3, 4, 6 and 24 hours at 30° C., the bacterial suspensions were taken and the supernatants were used to bioassay the AI produced. The data were means of four repeats.

To test the effect of Bt strains on quenching AI producing by pathogenic bacteria, *Erw. carotovora* SCG1 was co-cultured with Bt strains Cot1, B1, *E. coli* DH5α, and *B. fusiformis* respectively. AI was assayed as in Example 1. The AI produced by strain SCG1 was detected after 2 hours incubation, and a rapid increased was observed from 2 to 6 hours incubation (for cell numbers, see FIG. 14), whereas no AI was detected in the culture supernatant of SCG1 co-cultured with either Cot1 or B1 strain, which produce AI inactivation enzymes. In the co=culture supernatants of SCG1 with either *E. coil* DH5α or *B. fusiformis*, which do not contain aii genes, AI production levels were detected that were similar to those observed with SCG1 culture alone (FIG. 11). These results indicate that Bt strains effectively quench AI signals produced by the pathogen *Erw. carotovora* SCG1 when the two are cultured together.

EXAMPLE 8

Effect of Bt Strains on the Pathogenesis of *Erwinia carotovora*

It is known that AI play a key role in regulation of the virulence determinates of several pathogenic bacterial species. Since Bt strains effectively quenched AI signals produced by the pathogen, it is likely this new function of Bt strains can be exploited for disease control. To test this possibility, the effect of Bt strains for biocontrol against plant soft rot disease was investigated. Potato (*Solanum tuberosum* L. cv. Bintje) tubers were obtained from local stores. After rinsing in tap water and drying on paper towel, potato tubers were surface-sterilized with 70% ethanol, and then were sliced evenly to a 3 mm thickness. For the dip treatment, the potato slices were dipped into the bacterial suspension of Cot1, or other bacterial strains, diluted to a concentration of $5\times10^8$ colony forming unit (CFU) per ml, for about 20 seconds. Sterilised water was used as a control. The slices were dried in a laminar flow cabinet for about 20 min to remove surface moisture before inoculation with 2.5 μl of *Erw. carotovora* SCG1 bacterial suspension containing approximately $2\times10^8$ or $2\times10^7$, CFU/ml onto the top of each slice. For the mixture treatment, equal volumes of each testing organism ($5\times10^8$ CFU/ml), or sterile water were mixed with *Erw. carotovora* SCG1 bacterial suspension ($2\times10^8$ or $2\times10^7$ CFU/ml). The mixture (2.5 μl) was inoculated to a cut surface of the potato slices. All the potato slices were incubated in a Petri dish at 28° C. Maceration area was measured during incubation. Each treatment was repeated 4 to 12 time (12 for Cot1), each repeat was inoculated 3 places on one slice. For the colonisation experiment, each treatment was repeated 4 times, each tuber slice was inoculated only once at the centre of slice. Potato tuber slices were either treated with Bt strain Cot1 or other controls first before inoculation of *Erw. carotovora* SCG1, or SCG1 bacteria were mixed with Cot1 or other controls before inoculation onto potato slices.

Figure 12:
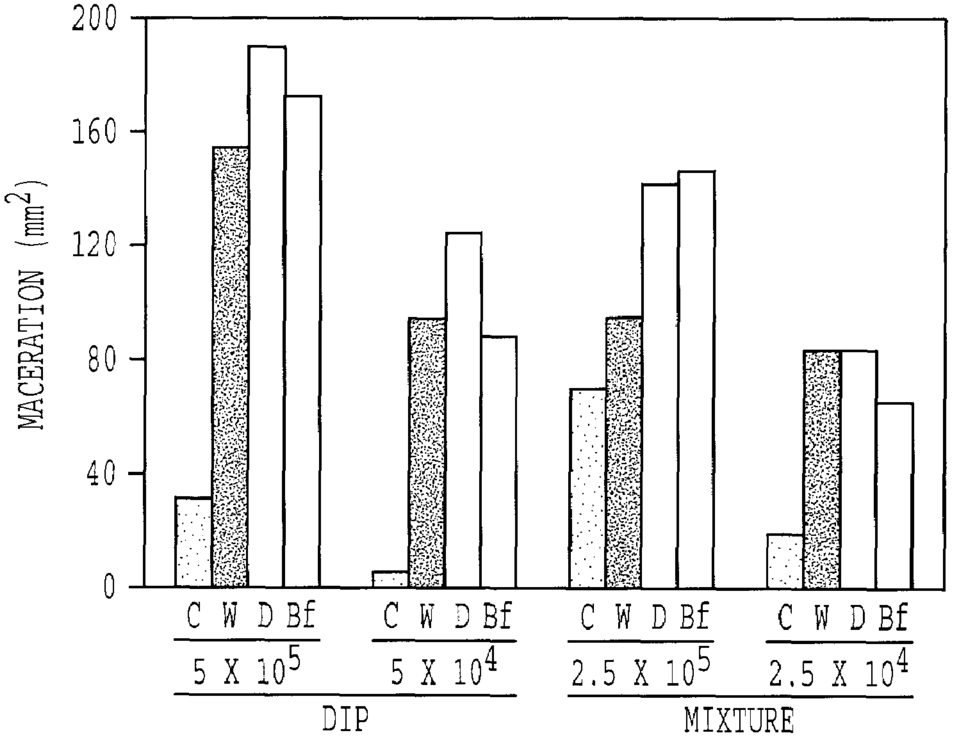
FIG. 12 shows the effect of Bt strain Cot1 on control of potato soft rot disease caused by *Erw. carotovora* SCG1. Dip: Potato slices were dipped into suspensions of Bt strain Cot1 (C), *E. coli* DH5α (D) or *B. fusiformis* (Bf) at a level of about $5\times10^8$ CFU/ml or water (W) for about 20 sec and then dried in a sterile air flow for about 20 min. The slices which showed no moisture on the surface were inoculated with 2.5 μl of bacterial suspension containing SCG1 cells equivalent to $5\times10^5$ or $5\times10^4$ CFU. Mixture: the cell culture of SCG1 ($2\times10^8$ or $2\times10^7$ CFU/ml) was mixed respectively with equal volumes of Cot1 (C), *E. coil* DH5α (D), *B. fusiformis* (Bf) ($5\times10^8$ CFU/ml) or water (W). Two point five microliters of the mixture was inoculated onto the top of slices. The final cell numbers of SCG1 inoculated are $2.5\times10^5$ or $2.5\times10^4$ CFU, as marked in the second line below the graph. After 20 hours incubation at 28° C. the maceration area was measured. The data were the means of 4 or 12 (12 for Cot1) repeats.

*Erw. carotovora* SCG1 caused severe tissue maceration of potato slices 20 hr after inoculation, whereas on Bt strain Cot1 pre-treated potato slices the maceration symptom was significantly attenuated (FIG. 12). Co-inoculation of SCG1 with the Bt strain Cot1 also attenuated soft rot symptoms, especially at the lower concentration of inoculum. In contrast, control treatments, either preteratment of potato slices with *E. coli* or *B. fusiformis* before inoculation of SCG1, or co-inoculation of SCG1 with *E. coli* and *B. fusiformis* respectively, showed severe tissue maceration symptoms (FIG. 12). These results suggest that Bt strains could be used as biocontrol agents against soft rot disease in plants.

EXAMPLE 9

In vitro Competition Between Bt Strain and *Erwinia carotovora* SCG1

The Bt strains Cot1 and B1 were tested for production antibiotics against *Erw. carotovora* SCG1. Competition experiments were conducted by co-inoculation of the Bt strain and *Erw. carotovora* in a 1:1 ratio. Each strain was inoculated at the level of about $1\times10^7$ CFU/ml for *Erw. carotovora* and $1\times10^6$ CFU/ml for other strains. The mixture was incubated at 30° C. At different time points the bacteria samples were taken for bioassay of AI production (the bioassay performed as in Example 1), and were diluted in suitable concentrations to spread on plates for colony counting. The experiment was repeated four times. For the colonisation experiment, the potato slices inoculated with *Erw. carotovora* were taken at times as indicated, and plant tissues about 15×15 mm circling the inoculation site were cut. The cut tissues were cut into small piece and placed in 10 ml of 0.1 M NaCl. After shaking for 30 min, the supernatant was diluted in suitable concentrations. Viable numbers of bacterial cells were counted.

Figure 13A:
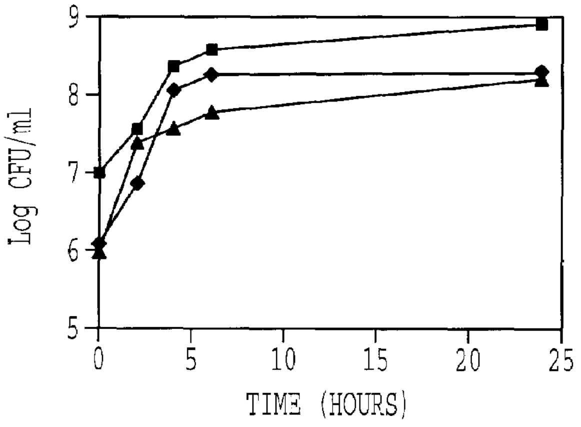
FIG. 13 shows the influence of Bt strains Cot1 and B1 on the growth of *Erwinia carotovora* SCG1. *Erw. carotovora* SCG1 (■) was inoculated alone or coinoculated with Bt strain Cot1 (♦) and B1 (▲) respectively in a 1:1 ratio in 15-ml LB medium. Each strain was inoculated to a final concentration of about $1\times10^7$ CFU/ml for SCG1 and $1\times10^6$ CFU/ml for the others in the $T_0$ medium. After 2, 4, 6 and 24 hours culture at 30° C., the bacterial suspensions were taken and diluted accordingly for spreading on plates for colony counting. The experiment was repeated four times and mean data were presented. Top: SCG1, Cot1, and B1 were incubated and grown separately; Middle: SCG1 was co-incubated with Cot1; Bottom: SCG1 was coincubated with B1.
Figure 13B:
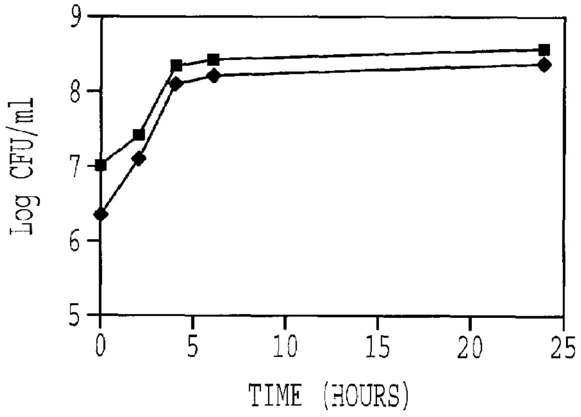
Figure 13C:
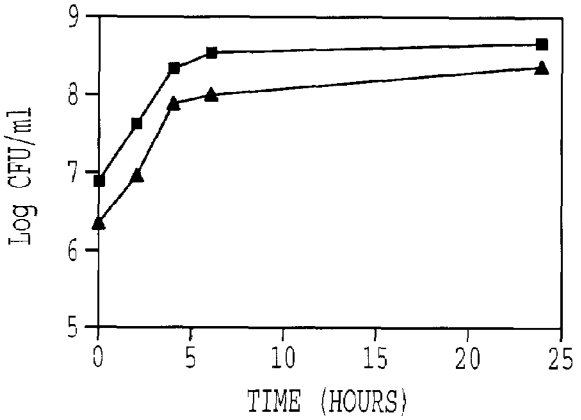

On plates of both rich and minimum media, Bt strains did not show any inhibitory effect on the growth of SCG1. When strain SCG1 and Bt strain Cot1 or B1 were coninoculated, both Bt strains and SCG1 grew normally, showing the same growth trend over a 24 hr period (FIG. 13).

EXAMPLE 10

Effect of Bt Strain on Colonisation of Tuber Slice by *Erwinia carotovora*

To investigate colonisation of *Erw. carotovora* SCG1 on potato slices after incubation, an expression vector containing the GFP gene was transformed into strain SCG1. The expression vector can be maintained in stain SCG1 stably without selection pressure. There was no difference in virulence between the SCG1 (GFP) and the wild-type SCG1. To investigate the effect of Bt bacteria on the survival and growth of SCG1 on plants, potato tuber slices were either dipped into bacterial suspensions of Cot1, then inoculated with SCG1

Figure 14A:
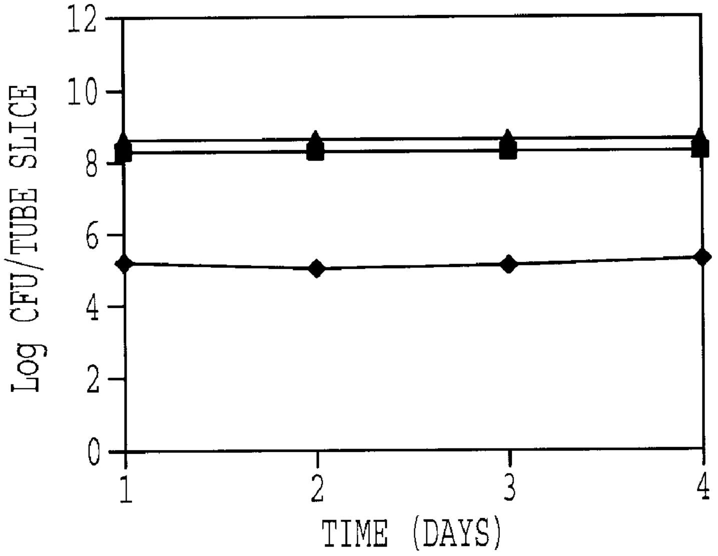
FIG. 14 shows changes in bacterial cell numbers (A) and development of soft rot symptom (B) on inoculated potato slices. Potato slices were dipped into Cot1 suspensions ($5\times10^8$ CFU/ml) (▲) or water (♦) for about 20 sec and then dried in a Laminar Flow for about 20 min. The slices were then inoculated with 5 μl of *Erw. carotovora* SCG1 ($2\times10^9$ CFU/ml). After incubation of 1, 2, 3 and 4 days at 28° C., the inoculated slices were cut into small pieces and 10 ml of 0.1 M NaCl solution was added for resuspension of bacterial cells. The mixture was shaken for 30 min and the suspension was diluted accordingly and spread on to plates for colony counting. The colony numbers of SCG1 were shown as log10 CFU/slice (▲ SCG1 only; ■ dipped in Cot1) and the numbers of Cot1 (♦) as log10 CFU/$mm^2$. The experiment was repeated four times and mean data were presented.
Figure 14B:
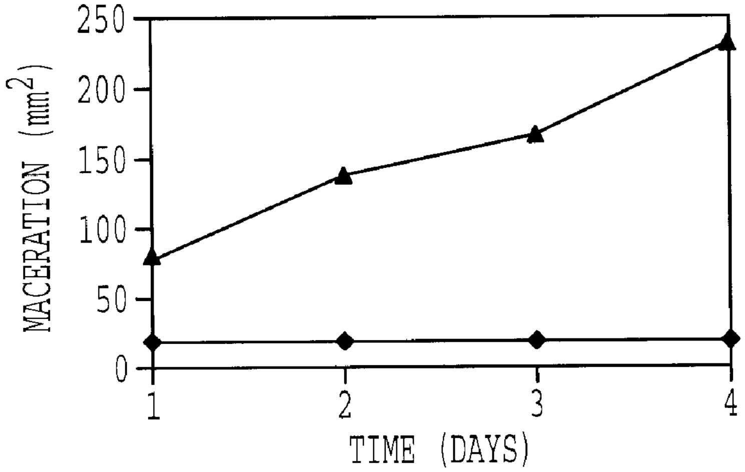

(GFP), or simultaneously inoculated with SCG1 (GFP) and Cot1. Changes in bacterial cell numbers and development of soft rotting symptoms of potato tissue were monitored daily for 4 days. Results showed that there were no big changes in cell numbers between SCG1 (GFP) on the Cot1-treated slices and the SCG1 (GFP) on the water-treated slices during 4-days incubation (FIG. 14). The result indicates that Bt strain Cot1 did not significantly affect the growth of SCG1 (GFP) on the potato tube slices, suggesting that attenuation of the virulence of *Erwinia* SCG1 (GFP) by Bt strain Cot1 was not due to inhibition of SCG1 (GFP) cell growth.

REFERENCES

Allison, D., Ruiz, B., SanJose, C., Jaspe, A., and Gilbert, P. (1998). Extracellular products as mediators of the formation and detachment of *Pseudomonas fluorescens* biofilms. FEMS Microbiol Lett 167, 179-184.

Bassler, B. L., Greenberg, E. P., and Stevens, A. M. (1997). Cross-species induction of luminescence in the quorum-sensing bacterium *Vibrio harveyi*. J Bacteriol 179, 4043-4045.

Beck von Bodman, S., and Farrand, S. K. (1995). Capsular polysaccharide biosynthesis and pathogenicity in *Erwinia stewartii* require induction by an N-acylhomoserine lactone autoinducer. J Bacteriol 177, 5000-5008.

Cao, J. G., and Meighen, E. A. (1989). J. Biol. Chem. 264, 21670-21676.

Cha, C., Gao, P., Chen, Y. C., Shaw, P. D., and Farrand, S. K. (1998). Production of acyl-homoserine lactone quorum-sensing signals by gram-negative plant-associated bacteria. Mol Plant Microbe Interact 11, 1119-1129.

Costa, J. M., and Loper, J. E. (1997). EcbI and EcbR: homologs of LuxI and LuxR affecting antibiotic and exoenzyme production by *Erwinia carotovora* subsp. *betavasculorum*. Can J Microbiol 43, 1164-1171.

Cronin, D., Moenne-Loccoz, Y., Fenton, A., Dunne, C., Dowling, D. N., and O'Gara, F. (1997). Ecological interaction of a biocontrol *Pseudomonas fluorescens* strain producing 2,4-diacetylphloroglucinol with the soft rot potato pathogen *Erwinia carotovora* subsp. *atrosetica*. FEMS Microbiol Ecology 23, 95-106.

Crowder, M. W., Maiti, M. K., Banovic, L., and Makaroff, C. A. (1997). Glyoxalase II from *A. thaliana* requires Zn(II) for catalytic activity. FEBS Lett 418, 351-354.

Davies, D. G., Parsek, M. R., Pearson, J. P., Iglewski, B. H., Costerton, J. W., and Greenberg, E. P. (1998). The involvement of cell-to-cell signals in the development of a bacterial biofilm. Science 280, 295-298.

Dong, Y.-H., Xu, J.-L., Li, X.-C., and Zhang, L.-H. (2000). AiiA, a novel enzyme inactivates acyl homoserine-lactone quorum-sensing signal and attenuates the virulence of *Erwinia carotovora*. Proc. Natl. Acad. Sci. USA 97: 3526-3531.

Dumenyo, C. K. M., Chun, A. W., and Chatterjee, A. K. (1998). Genetic and physiological evidence for the production of N-acyl homoserine lactones by *Pseudomonas syringae* pv. *syringae* and other fluorescent plant pathogenic *Pseudomonas* species. Eur J Plant Pathol 104, 569-582.

Dunphy, G., Miyamoto, C., and Meighen, E. (1997). A homoserine lactone autoinducer regulates virulence of an insect-pathogenic bacterium, *Xenorhabdus nematophilus* (*Enterobacteriaceae*). J Bacteriol 179, 5288-5291.

Eberhard, A., Burlingame, A. L., Eberhard, C., Kenyon, G. L., Nealson, K. H., and Oppenheimer, N. J. (1981). Biochemistry 20, 2444-2449.

Eberl, L., Winson, M. K., Sternberg, C., Stewart, G. S. A. B., Christiansen, G., Chhabra, S. R., Bycroft, B., Williams, P., Molin, S., and Givoskov, M. (1996). Involvement of N-acyl-L-homoserine lactone autoinducers in controlling the multicellular behaviour of *Serratia liquefaciens*. Mol Microbiol 20, 127-136.

Emmert, E. A. B., and Handelsman, J. (1999). Biocontrol of plant disease: a (Gram-) positive perspective. FEMS Microbiol Lett 171, 1-9.

Feitelson, J. S., Payne, J., and Kim L. (1992). *Bacillus thuringiensis*: insects and beyond. Bio/Technology 10, 271-275.

Flavier, A. B., Schell, M. A., and Denny, T. P. (1998). An RpoS (sigmaS) homologue regulates acylhomoserine lactone-dependent autoinduction in *Ralstonia solanacearum*. Mol Microbiol 28, 475-86.

Fuqua, C., and Winans, S. C. (1996). Conserved cisacting promoter elements are required for density-dependent transcription of *Agrobacterium tumefaciens* conjugal transfer genes. J Bacteriol 178, 435-40.

Garfinkel, D. J., and Nester, E. W. (1980). *Agrobacterium tumefaciens* mutants affected in crown gall tumorigenesis and octopine catabolism. J Bacteriol 144, 732-43.

Jones, S. M., Yu, B., Bainton, N. J., Birdsall, M., Bycroft, B. W., Chhabra, S. R., Cox, A. J. R., Golby, P., Reeves, P. J., Stephens, S., Winson, M. K., Salmond, G. P. C., Stewart, G. S. A. B., and Williams, P. (1993). The Lux autoinducer regulates the production of exoenzyme virulence determination in *Erwinia carotovora* and *Pseudomonas aeruginosa*. EMBO J 12, 2477-2482.

Lambert, B., and Peferoen, M. (1992). Insecticidal promise of *Bacillus thuringiensis*. Facts and mysteries about a successful biopesticide. BioScience 42, 112-122.

Liao, C.-H., and Sapers, G. M. (1999). Influence of soft rot bacteria on growth of *Listeria monocytogenes* on potato tuber slices. J Food Prot 62, 343-348.

Lin, H. C., Lei, S. P., and Wilcox, G. (1985). An improved DNA sequencing strategy. Anal Biochem 1985 May 15; 147(1):114-9 147, 114-119.

Nasser, W., Bouillant, M. L., Salmond, G., and Reverchon, S. (1998). Characterization of the *Erwinia chrysanthemi* expl-expR locus directing the synthesis of two N-acyl-homoserine lactone signal molecules. Mol Microbiol 29, 1391-1405.

Passador, L., Cook, J. M., Gambello, M. J., Rust, L., and Iglewski, B. H. (1993). Expression of *Pseudomonas aeruginosa* virulence genes requires cell-to-cell communication. Science 260, 1127-1130.

Pearson, J. P., Gray, K. M., Passador, L., Tucker, K. D., Eberhard, A., Iglewski, B. H., and Greenberg, E. P. (1994). Structure of the autoinducer required for expression of *Pseudomonas aeruginosa* virulence genes. Proc Natl Acad Sci USA 91, 197-201.

Piper, K. R., Beck von Bodman, S., and Farrand, S. K. (1993). Conjugation factor of *Agrobacterium tumefaciens* regulates Ti plasmid transfer by autoinduction. Nature 362, 448-450.

Pirhonen, M., Flego, D., Heikinheimo, R., and Palva, E. (1993). A small diffusible signal molecule is responsible for the global control of virulence and exoenzyme production in the plant pathogen *Erwinia carotovora*. EMBO J 12, 2467-2476.

Sambrook, J. F., Fritsch, E. F., and Maniatis, T. (1989). Molecular Cloning: A laboratory manual (New York: Cold Spring Harbor Laboratory Press).

Simon, R., Priefer, U., and Pühler, A. (1983). A broad host range mobilization system for in vivo genetic engineering: transposon mutagenesis in Gram-negative bacteria. Bio/Technol. November, 784-791.

Staskawicz, B. D., Keen, N. T., and Napoli, C. (1987). Molecular characterization of cloned avirulence genes from race 0 and race 1 of *Pseudomonas syringae* pv. *glycinea*. J Bacteriol 169, 5789-5794.

Vallee, B. L., and Galdes, A. (1984). The metallobiochemistry of zinc enzymes. Adv Enzymol Relat Areas Mol Biol 56, 283-430.

Zhang, L.-H. (1993). Molecular biology and biochemistry of a novel conjugation factor in *Agrobacterium. Doctoral Dissertation*, The Adelaide University, Australia.

Zhang, L.-H., Xu, J., and Birch, R. G. (1998). High affinity binding of albicidin phytotoxins by the AlbA protein from *Klebsiella oxytoca*. Microbiol 144, 555-559.

Zhang, L.-H., and Kerr, A. (1991). A diffusible compound can enhance conjugal transfer of the Ti plasmid in *Agrobacterium tumefaciens*. J Bacteriol 173, 1867-1872.

Zhang, L.-H., Murphy, P. J., Kerr, A., and Tate, M. E. (1993). *Agrobacterium* conjugation and gene regulation by N-acyl-L-homoserine lactones. Nature (London) 362, 446-447.

The invention claimed is:

1. An isolated nucleic acid molecule encoding a protein comprising 263 amino acids having the formula 102aa-amino acid motif-61aa, wherein the amino acid motif consists of HXHXDH-71aa-H-21aa-D, wherein said protein has autoinducer inactivation activity and wherein the protein has the amino acid sequence set forth in SEQ ID NO:11.

2. The isolated nucleic acid molecule of claim 1, wherein the nucleic acid molecule has the nucleotide sequence set forth in SEQ ID NO:1.

3. An expression vector comprising the nucleic acid molecule of claim 1.

4. An expression vector comprising the nucleic acid molecule of claim 2.

5. An isolated protein comprising 263 amino acids having the formula 102aa-amino acid motif-61aa, wherein the amino acid motif consists of HXHXDH-71aa-H-21aa-D, wherein said protein has autoinducer inactivation activity and wherein the protein has the amino acid sequence set forth in SEQ ID NO:11.

6. A method of reducing bacterial damage to a plant or animal, which method comprises administering to a plant or animal in need of such reduction an effective amount of the protein of claim 5.

7. A method according to claim 6, wherein administration is to an animal.

8. A method according to claim 7, wherein the animal is a human.

9. An isolated cell of a procaryote or eukaryote stably transformed with a nucleic acid molecule encoding a protein comprising 263 amino acids having the formula 102aa-amino acid motif-61aa, wherein the amino acid motif consists of HXHXDH-71aa-H-21aa-D, wherein said protein has autoinducer inactivation activity and wherein the protein has the amino acid sequence set forth in SEQ ID NO:11.

10. The isolated cell of claim 9, wherein the nucleic acid molecule has the nucleotide sequence set forth in SEQ ID NO:1.

* * * * *